US009321828B2

(12) United States Patent
Zhang et al.

(10) Patent No.: US 9,321,828 B2
(45) Date of Patent: Apr. 26, 2016

(54) NON-GLYCOSYLATED TRANSFERRIN EXPRESSED IN MONOCOTS

(75) Inventors: Deshui Zhang, Woodland, CA (US); Ning Huang, Davis, CA (US); Diane Phuong Nguyen, Elkgrove, CA (US); Paula Bryan, Dublin, CA (US)

(73) Assignee: Ventria Bioscience Inc., Fort Collins, CO (US)

( * ) Notice: Subject to any disclaimer, the term of this patent is extended or adjusted under 35 U.S.C. 154(b) by 328 days.

(21) Appl. No.: 13/102,966

(22) Filed: May 6, 2011

(65) Prior Publication Data

US 2012/0088729 A1 Apr. 12, 2012

Related U.S. Application Data

(60) Provisional application No. 61/332,733, filed on May 7, 2010.

(51) Int. Cl.

| | |
|---|---|
| ***A01H 5/00*** | (2006.01) |
| ***A01H 5/10*** | (2006.01) |
| ***C12N 15/09*** | (2006.01) |
| ***C12N 15/82*** | (2006.01) |
| ***C12N 15/12*** | (2006.01) |
| ***C12N 5/00*** | (2006.01) |
| ***A61K 38/00*** | (2006.01) |
| ***A61K 38/40*** | (2006.01) |
| ***C07K 14/79*** | (2006.01) |

(52) U.S. Cl.

CPC ............ *C07K 14/79* (2013.01); *C12N 15/8257* (2013.01); *A61K 38/40* (2013.01); *C07K 2319/02* (2013.01)

USPC ...... 800/288; 800/320.2; 435/69.1; 435/69.6; 435/468; 435/389; 435/419; 536/23.5; 514/5.4

(58) Field of Classification Search

None

See application file for complete search history.

(56) References Cited

U.S. PATENT DOCUMENTS

| | | | | |
|---|---|---|---|---|
| 6,991,824 | B2 | 1/2006 | Huang et al. | |
| 7,417,178 | B2 | 8/2008 | Huang et al. | |
| 7,589,252 | B2 | 9/2009 | Huang et al. | |
| 8,158,857 | B2 | 4/2012 | Huang et al. | |
| 2003/0056244 | A1 | 3/2003 | Huang et al. | |
| 2005/0054043 | A1 * | 3/2005 | Funk et al. | 435/69.1 |
| 2008/0050503 | A1 * | 2/2008 | Huang et al. | 426/629 |
| 2008/0318277 | A1 | 12/2008 | Huang et al. | |
| 2009/0156486 | A1 | 6/2009 | Huang et al. | |
| 2009/0258004 | A1 | 10/2009 | Huang et al. | |
| 2010/0031394 | A1 | 2/2010 | Huang et al. | |
| 2010/0119691 | A1 | 5/2010 | Huang et al. | |
| 2010/0183589 | A1 | 7/2010 | Huang et al. | |

OTHER PUBLICATIONS

Hwang et al (Plant Cell Physiol., 45(10), pp. 1509-1518, 2004).*

Shmidt et al (Proc. Natl. Acad. Sci., 87, pp. 46-50, 1990).*

Lienard et al (Biotechnology Annual Review, 13, pp. 115-147, 2007).*

Fujiyama et al (Bioscience, Biotechnology, and Biochemistry, 68(12), pp. 2565-2570, 2004).*

Zhang et al (Protein Expr. Purif. 74(1), pp. 69-79, 2010); cited on IDS.*

UniProt B1Q146—MACCY (published in UniProt Apr. 2008).*

Ali et al., "High-yield production of functionally active human serum transferrin using a baculovirus expression system, and its structural characterization", Biochem. J., vol. 319, Prt. 1, pp. 191-195 (1996).

Bai et al., "Recombinant granulocyte colony-stimulating factor-transferrin fusion protein as an oral myelopoietic agent", PNAS USA, vol. 102, No. 20, pp. 7292-7296 (2005).

Baker et al., "Dealing with iron: common structural principles in proteins that transport iron and heme", PNAS USA, vol. 100, No. 7, pp. 3579-3583 (2003).

Banerjee et al., "Transferrin receptors in the human gastrointestinal tract. Relationship to body iron stores", Gastroentrerology, vol. 91, No. 4, pp. 861-869 (1986).

Barnes et al., "Serum-free cell culture: a unifying approach", Cell, vol. 22, No. 3, pp. 649-655 (1980).

Castilho et al., "Construction of a functional CMP-sialic acid biosynthesis pathway in *Arabidopsis*", Plant Physiol., vol. 147, No. 1, pp. 331-339 (2008).

Cheng et al., "Structure of the human transferrin receptor-transferrin complex", Cell, vol. 116, No. 4, pp. 565-576 (2004).

Cheng et al., "Single particle reconstruction of the human apo-transferrin-transferrin receptor complex", J. Struct. Biol., vol. 152, No. 3, pp. 204-210 (2005).

Chikwamba et al., "A functional antigen in a practical crop: LT-B producing maize protects mice against *Escherichia coli* heat labile enterotoxin (LT) and cholera toxin (CT)", Transgenic Res., vol. 11, No. 5, pp. 479-493 (2002).

Danielle et al., "Medical molecular farming: production of antibodies, biopharmaceuticals and edible vaccines in plants", Trends Plant Sci., vol. 6, No. 5, pp. 219-226 (2001).

Evans et al., "The electrophoresis of transferrins in urea/polyacrylamide gels", Biochem. J., vol. 189, No. 3, pp. 541-546 (1980).

Farran et al., "Targeted expression of human serum albumin to potato tubers", Transgenic Res., vol. 11, pp. 337-346 (2002).

Fischer et al., "Plant-based production of biopharmaceuticals", Curr. Opin. Plant Biol., vol. 7, No. 2, pp. 152-158 (2004).

Fu et al., "N-glycosylation site mapping of human serotransferrin by serial lectin affinity chromatography, fast atom bombardment-mass spectrometry, and 1H nuclear magnetic resonance spectroscopy", Anal. Biochem., vol. 206, No. 1, pp. 53-63 (1992).

He et al., "Molecular aspects of release of iron from transferrin", Templeton, ed., *Molecular and Cellular Iron Transport*, CRC Press, pp. 95-124 (2002).

Hentze et al., "Balancing acts: molecular control of mammalian iron metabolism", Cell, vol. 117, No. 3, pp. 285-297 (2004).

Hirose, "The structural mechanism for iron uptake and release by transferrins", Biosci. Biotechnol. Biochem., vol. 64, No. 7, pp. 1328-1336 (2000).

(Continued)

*Primary Examiner* — Anne Kubelik

*Assistant Examiner* — Stephen Uyeno

(74) *Attorney, Agent, or Firm* — Susan J. Myers Fitch; SJ Myers Fitch, Patent Agent, LLC

(57) ABSTRACT

Disclosed are compositions and methods of making non-glycosylated transferrin protein in transgenic monocot plants.

18 Claims, 10 Drawing Sheets

(56) References Cited

OTHER PUBLICATIONS

Hoefkens et al., "Isolation, renaturation and partial characterization of recombinant human transferrin and its half molecules from *Escherichia coli*", Int. J. Biochem. Cell Biol., vol. 28, No. 9, pp. 975-982 (1996).

Hoefkens et al., "Influence of transferrin glycans on receptor binding and iron-donation", Glycoconj. J., No. 14, No. 2, vol. 289-295 (1997).

Hood et al., "Commercial production of avidin from transgenic maize: characterization of transformant, production, processing, extraction and purification", Molecular Breeding, vol. 3, pp. 291-306 (1997).

Huang et al., "Structural organization and differential expression of rice alpha-amylase genes", Nucleic Acids Res., vol. 18, No. 23, pp. 7007-7014 (1990).

Huang et al., "The tissue-specific activity of a rice beta-glucanase promoter (Gns9) is used to select rice transformants", Plant Science, vol. 161, pp. 589-595 (2001).

Huang et al., "Expression of natural antimicrobial human lysozyme in rice grains", Molecular Breeding, vol. 10, Issue 1-2, pp. 83-94 (2002).

Huang et al., "ExpressTec: High level expression of biopharmaceuticals in cereal grains", K.J., ed., Modern Biopharm., Wiley VCH, pp. 931-947, (2005).

Laskey et al., "Evidence that transferrin supports cell proliferation by supplying iron for DNA synthesis", Exp. Cell. Res., vol. 176, No. 1, pp. 87-95 (1988).

Li et al., "Transferrin/transferrin receptor-mediated drug delivery", Med. Res. Rev., vol. 22, No. 3, pp. 225-250 (2002).

Lienard et al., "Pharming and transgenic plants", Biotechnol. Annu. Rev., vol. 13, pp. 115-147 (2007).

MacGillivray et al., "The primary structure of human serum transferrin. The structures of seven cyanogen bromide fragments and the assembly of the complete structure", J. Biol. Chem., vol. 258, No. 6, pp. 3543-3553 (1983).

MacGillivray et al., "Transferrins", Templeton, ed., Molecular and Cellular Iron Transport, Marcel Dekker, New York, pp. 41-70 (2002).

Makey et al., "The detection of four molecular forms of human transferrin during the iron binding process", Biochem. Biophys. Acta., vol. 453, No. 1, pp. 250-256 (1976).

Mason et al., "Expression, purification, and characterization of authentic monoferric and apo-human serum transferrins", Protein Expr. Purif., vol. 36, No. 2, pp. 318-326 (2004).

Mortellaro et al., "Advance in animal-free manufacturing of biopharmaceuticals, New recombinant raw ingredients developed for use in large-scale mammalian cell culture are becoming readily available", BioPharm International.com, 8 pgs., (2007) Online article downloaded from http://www.biopharminternational.com/biopharm/Upstream+Processing/Advances-in-Animal-Free-Manufacturing-of-Biopharma/ArticleStandard/Article/detail/423195 on Dec. 3, 2013.

Nandi et al., "Process development and economic evaluation of recombinant human lactoferrin expressed in rice grain", Transgenic Res., vol. 14, No. 3, pp. 237-249 (2005).

Nandi et al., "Expression of human lactoferrin in transgenic rice grains for the application in infant formula", Plant Sci., vol. 163, No. 4, pp. 713-722 (2002).

Okita et al., "Structure and expression of the rice glutelin multigene family", J. Biol. Chem., vol. 264, No. 21, pp. 12573-12581 (1989).

Pardridge, "Molecular Trojan horses for blood-brain barrier drug delivery", Discov. Med., vol. 6, No. 34, pp. 139-143 (2006).

Qian et al., "Targeted drug delivery via the transferrin receptor-mediated endocytosis pathway", Pharmacol. Rev., vol. 54, No. 4, pp. 561-587 (2002).

Qu et al., "Evaluation of tissue specificity and expression strength of rice seed component gene promoters in transgenic rice", Plant Biotechnol. J., vol. 2, No. 2, pp. 113-125 (2004).

Sargent et al., "Characterisation of recombinant unglycosylated human serum transferrin purified from *Saccharomyces cerevisiae*", BioMetals, vol. 19, No. 5, pp. 513-519 (2006).

Sharath et al., "Human immunoglobulin biosynthesis in a serum-free medium", J. Lab Clin. Med., vol. 103, No. 5, pp. 739-748 (1984).

Soni et al., "Potential of transferrin and transferrin conjugates of liposomes in drug delivery and targeting", Am. J. Drug Del., vol. 3, pp. 155-170 (2005).

Stoger et al., "Cereal crops as viable production and storage systems for pharmaceutical scFv antibodies", Plant Mol. Biol., vol. 42, No. 4, pp. 583-590 (2000).

Twyman et al., "Transgenic plants in the biopharmaceutical market", Expert Opin. Emerg. Drugs, vol. 10, No. 1, pp. 185-218 (2005).

Wally et al., "A structural comparison of human serum transferrin and human lactoferrin", Biometals, vol. 20, No. 3-4, pp, 249-262 (2007).

Widera et al., "Mechanisms of TfR-mediated transcytosis and sorting in epithelial cells and applications toward drug delivery", Adv. Drug. Deliv. Rev., vol. 55, No. 11, pp. 1439-1466 (2003).

Wilken et al., "Factors influencing recombinant human lysozyme extraction and cation exchange adsorption", Biotechnol. Prog., vol. 22, No. 3, 745-752 (2006).

Williams et al., "The distribution of iron between the metal-binding sites of transferrin human serum", Biochem. J., vol. 185, No. 2, pp. 483-488 (1980).

Williams, "The evolution of transferrin", Trends Biochem. Soc., vol. 7, pp. 394-397 (1982).

Zak et al., "Nonrandom distribution of iron in circulating human transferrin", Blood, vol. 68, No. 1, pp. 157-161 (1986).

Zeleny et al., "Sialic acid concentrations in plants are in the range of inadvertent contamination", Planta, vol. 224, No. 1, pp. 222-227 (2006).

Zhang, et al., "Expresion, purification, and characterization of recombinant human transferrin from rice (Oryza sativa L.)" Prot. Expr. Purif. Nov. 2010. 74(1):69-79.

* cited by examiner

Gt1 Promoter SP hTF T-NOS

"Gt1 promoter" = rice seed storage protein glutelin gene promoter; "SP" = Gt1 signal peptide; "hTF" = human transferrin; "T-Nos" = nopaline synthase gene terminator of *Agrobacterium tumefaciens*.

Immuno dot-blot expression of hTF in transgenic rice seeds.

SDS-PAGE (A) and Western blot (B) analysis of rhTF expressed in rice grain.

Tissue specificity of rhTF expression in rice. SDS-PAGE gel(A) and western blot immuno-detection with anti-hTF antibody (B).

FIG.5

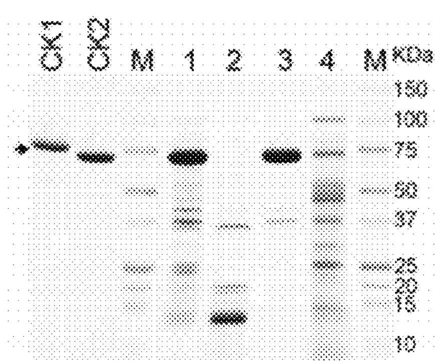

SDS-PAGE of DEAE-Sepharose column fractionation of protein extracts from rice-expressed rhTF. Lanes CK1 and CK2 = native hTF (Sigma) and yeast-derived aglycosylated rhTF (Millipore), respectively. M = molecular weight marker; lane 1= crude grain extract containing rhTF; lane 2 = flow-through; lane 3 = eluate; lane 4 = high salt fraction after the elution of rhTF; arrowhead indicates hTF.

MALDI mass spectra of purified rice-derived rhTF.

PNGase F treatment of rice-derived rhTF. M, molecular weight marker; 1, 2, and 3, represent native hTF (Sigma), rice-derived rhTF, and yeast-derived aglycosylated rhTF (Millipore), respectively. + and -, represent with and without PNGase F treatment, respectively.

Isoelectric focusing gel analysis of rice-derived rhTF.

RP-HPLC comparison of rice-derived rhTF and nhTF.

Iron-binding characteristics of rice-derived rhTF.
(A) = Color appearance of rhTF with different iron saturation levels.
(B) = urea-PAGE gel analysis.
1A & 1B = partially-iron-saturated (pis) rhTF; 2A & 2B = apo-rhTF made from purified pis- rhTF; 3A & 3B = holo-rhTF made from apo-rhTF.
(C) = comparison of rice-derived rhTF with commercial sources of hTF.

visible spectra of rhTF in response to different concentrations of ferric iron.

Effect of rhTF on cell growth and antibody production.

NON-GLYCOSYLATED TRANSFERRIN EXPRESSED IN MONOCOTS

CROSS-REFERENCE TO RELATED APPLICATIONS

This application claims priority, pursuant to 35 U.S.C. §119 (e), to the filing date of U.S. Provisional Patent Application Ser. No. 61/332,733 filed 7 May 2010, the disclosure of which is herein incorporated by reference in its entirety.

STATEMENT REGARDING FEDERALLY SPONSORED RESEARCH

This work was supported in part with government support under NIH grant GM086916 from the National Institute of General Medical Sciences. The United States government may have rights to certain aspects of the disclosure.

REFERENCE TO SEQUENCE LISTING, TABLE OR COMPUTER PROGRAM

The instant application includes a sequence listing in the form of a text file created 6 May 2011, named "506658035US00SeqList.txt" (63488 bytes) as well as submitted in the form of a paper copy, each of which is incorporated into the application by reference in its entirety.

INTRODUCTION

The present teachings relate to monocot seeds and seed compositions containing levels of transferrin protein between 3-40% or higher of the total protein weight of the soluble protein extractable from the seed, and methods of producing high levels of non-glycosylated transferrin protein in transgenic monocots, for use in making a serum-free cell culture medium, as well as animal, in particular human, therapeutic compositions.

BACKGROUND

Iron is an element used by eukaryotic organisms and most microorganisms as a cofactor of numerous proteins or enzymes for respiration, DNA synthesis, and many other critical metabolic processes (Baker, et al., *Proc Natl Acad Sci USA* 100: 3579-3583 (2003)). Cellular iron deficiency can arrest cell proliferation and even cause cell death, whereas the excessive iron will be toxic to cells by reacting with oxygen via the Fenton reaction to produce highly reactive hydroxyl radicals that cause oxidative damage to cells (Baker, et al., *Proc Natl Acad Sci USA* 100: 3579-3583 (2003); Hentze, M. U., et al., *Cell* 117: 285-97(2004)). To overcome the dual challenges of iron deficiency and overload, a family of iron carrier glycoproteins collectively called transferrins has evolved in nearly all organisms to tightly control cellular iron uptake, storage, and transport to maintain cellular iron homeostasis (Williams, J., *Trends Biochem. Soc.* 7: 394-397 (1982)). The transferrin protein family includes several homologous glycoproteins generally having a molecular weight of approximately 80 kDa and an ability to bind iron, and is divided into four subsets: (1) serum transferrins (TF) which have a role in iron transport in the body; (2) lactoferrins (LF) found in mammalian extracellular secretions such as milk, tears, pancreatic fluid and other bodily secretions of mammals; (3) melanotransferrins (mTF) which is present on the surface of melanocytes and in liver and intestinal epithelium; and (4) ovotransferrins (oTF) found in bird and reptile oviduct secretions and egg white. While all members of the transferrin protein family can bind iron to control free iron level, human serum transferrin provides both a means of transporting iron from the sites of absorption and storage to the sites of utilization, as well as protection against the damaging effects of iron-catalyzed free radicals. To date, only TF has been proven to be able to transport iron to cells (Baker, et al., *Proc Natl Acad Sci USA* 100: 3579-3583 (2003)).

One exemplary TF is a single-chain glycoprotein of 679 amino acid residues including 38 cysteine residues which are all disulfide bonded. TF consists of two homologous halves, each comprising about 340 amino acid residues and sharing about 40% sequence identity (Baker, et al., *Proc Natl Acad Sci USA* 100: 3579-3583 (2003); Hirose, *Biosci. Biotechnol. Biochem.* 64:1328-1336 (2000); J. Wally, et al., *Biometals* 20: 249-62 (2007)). The two homologous halves are shown by X-ray crystallography to fold into two distinct globular lobes called N- and C-terminal lobes (Baker, et al., *Proc Natl Acad Sci USA* 100: 3579-3583 (2003); Hirose, *Biosci. Biotechnol. Biochem.* 64:1328-1336 (2000)). Each lobe comprises two dissimilar domains (N1 and N2 in the N-lobe; C1 and C2 in the C-lobe) separated by a deep cleft, where the iron binding site is located. The iron-binding ligands in each lobe are identical, which involves the side chains of an aspartic acid, two tyrosines, a histidine and two oxygen molecules from a synergistic carbonate anion (Baker, et al., *Proc Natl Acad Sci USA* 100: 3579-3583 (2003); Hentze, M. U., et al., *Cell* 117: 285-97(2004); Hirose, *Biosci. Biotechnol. Biochem.* 64:1328-1336 (2000); J. Wally, et al., *Biometals* 20: 249-62 (2007); Q.-Y. He, et al., "Molecular aspects of release of iron from transferrin," in: D. M. Templeton, (Ed.), *Molecular and Cellular Iron Transport*, CRC Press, 2002, pp. 95-124).

The cellular iron uptake and transport is normally driven by a TF/TF receptor (TFR)-mediated endocytotic process (Baker, et al., *Proc Natl Acad Sci USA* 100: 3579-3583 (2003)). When TF is free of iron (apo-TF), both its N- and C-lobes adopt an open conformation through keeping two domains in each lobe well separated for easy access of the ferric iron. At the extracellular pH of 7.4, the apo-TF binds one (monoferric TF) or two iron molecules (diferric TF or holo-TF) by the coordination of iron-binding ligands. The diferric TF then binds to TFR on the cell surface in a way that the TF C-lobe binds laterally at the helical domain of dimeric TFR while the TF N-lobe is sandwiched between the TFR ectodomain and the cell membrane (Cheng, et al., *Cell* 116: 565-76 (2004); Cheng, et al., *J. Struct. Biol.* 152: 204-210 (2005)). This TF-TFR complex is then endocytosed into the early endosome, where the acidic environment (pH 5.5) triggers the conformational change of TF-TFR and the subsequent release of iron from TF by first protonating and dissociating the synergistic anion followed by protonating iron binding-related His and/or Tyr ligands (Baker, et al., *Proc Natl Acad Sci USA* 100: 3579-3583 (2003); Q.-Y. He, et al., "Molecular aspects of release of iron from transferrin," in: D. M. Templeton, (Ed.), *Molecular and Cellular Iron Transport*, CRC Press, 2002, pp. 95-124). Finally, the apo-TF-TFR complex is recycled to the cell surface, where the neutral extracellular pH will dissociate the complex and release the TF for re-use.

The TF-TFR complex-mediated endocytosis pathway for iron transport is not only biologically significant for maintaining cellular iron homeostasis, but also has important pharmaceutical applications. TF is also an important ingredient of serum-free cell culture media due to its role in regulating cellular iron uptake, transport, and utilization in cultured cells. TF in serum-free cell culture medium ensures iron delivery to propagating cells for sustained growth in mammalian culture for the production of therapeutic proteins and vaccines (Barnes, et al., *Cell* 22: 649-55 (1980); Laskey, et al., *Exp. Cell Res.* 176: 87-95 (1988); Mortellaro, et al., *Biopharm. International* 20 (Supp) 30-37 (2007); Sharath, et al., *J Lab Clin Med* 103: 739-48 (1984)).

In addition, TF has also been actively pursued as a drug-delivery vehicle. As a drug carrier, TF increases a drug's therapeutic index via its unique transferrin receptor-mediated endocytosis pathway, as well as its added advantages of being biodegradable, nontoxic, and nonimmunogenic (Qian, et al., *Med. Res. Rev.* 22: 225-50 (2002); Qian, et al., *Pharmacol. Rev.* 54: 561-87 (2002); Soni, et al., *American Journal of Drug Delivery* 3: 155-70 (2005)). TF not only can deliver anti-cancer drugs to primary proliferating malignant cells where the TF is abundantly expressed (Qian, et al., *Pharmacol. Rev.* 54: 561-87 (2002)), but also can deliver drugs to the brain by crossing the blood-brain barrier (BBB), which is a major barrier for administrating sufficient drugs to reach the central nervous system (CNS) (Qian, et al., *Med. Res. Rev.* 22: 225-50 (2002); Soni, et al., *American Journal of Drug Delivery* 3: 155-70 (2005); Pardridge, *Discov. Med.* 6:139-43 (2006)). TF can also be exploited for oral delivery of protein-based therapeutics (Bai, et al., *Proc. Natl. Acad. Sci. U.S.A.* 102: 7292-6 (2005); Widera, et al., *Adv. Drug Deliv. Rev.* 55:1439-66(2003)), as TF is resistant to proteolytic degradation and TFR is abundantly expressed in human gastrointestinal (GI) epithelium (Bai, et al., *Proc. Natl. Acad. Sci. U.S.A.* 102: 7292-6 (2005); Banerjee, et al., *Gastroenterology* 91: 861-9 (1986)).

With the increasing concerns over the risk of transmission of infectious pathogenic agents from the use of human or animal plasma-derived TFs in both cell culture and drug delivery applications, recombinant transferrin (rTF) is preferred to native TF (Keenan, et al., *Cytotechnology* 51: 29-37 (2006)). Recombinant human TF (rhTF) has long been pursued in a variety of expression systems (MacGillivray, et al., "Transferrins" in: D. M. Templeton, (Ed.), *Molecular and cellular iron transport*, Marcel Dekker, New York, 2002, pp. 41-70), but proves to be challenging largely due to hTF's complicated structural characteristics as described above. The commonly used *E. coli* system for production of recombinant proteins has proved to be impractical for producing rhTF, as the expressed rhTF protein remains in insoluble inclusion bodies and the yield of functionally active rhTF after renaturation is very limited (Hoefkens, et al., *Int. J. Biochem. Cell Biol.* 28: 975-82 (1996)). Although both the insect cell (baculovirus) (Ali, et al., *Biochem. J.* 319 (Pt 1):191-5 (1996)) and mammalian cell (MacGillivray, et al., "Transferrins" in: D. M. Templeton, (Ed.), *Molecular and cellular iron transport*, Marcel Dekker, New York, 2002, pp. 41-70) expression systems have been shown to be able to express the bioactive rhTF, neither of them express at high enough levels to provide enough quantity to be a feasible source of commercial production, as well as being cost prohibitive.

It is shown herein that when transferrin is expressed in bacterial, yeast, mammalian cells, and insect cell expression systems, the expressed native transferrin protein bears a glycosylation pattern characteristic of the host organism, i.e., animal cell-expressed transferrin has a animal-type glycosylation pattern, and yeast-expressed transferrin has a yeast-type glycosylation pattern. It is desirable to produce a biologically active transferrin protein that is non-glycosylated for therapeutic use, to avoid possible allergic or immunological reactivity. Recently, bioactive rhTF was expressed in *Saccharomyces cerevisiae* using a mutated transferrin gene in which two of its N-linked glycosylation sites have been knocked out, and this rhTF became commercially available. (Sargent, et al., *BioMetals* (2006) 19:513-519). However, this yeast-derived rhTF, still remains very expensive to produce (Millipore, Billerica, Mass.). To address the problems of the shortage and the high cost of producing rhTF, as well as to meet a previously unmet need for producing high levels of an non-glycosylated human transferrin, alternative expression systems are desirable.

With the advancement of plant molecular biology in general and the improvement of plant transformation techniques in particular, plant hosts have become a powerful system to produce recombinant proteins cost-effectively and on a large scale (Daniell, et al., *Trends Plant Sci.* 6: 219-26 (2001); Lienard, et al., *Biotechnol. Annu. Rev.* 13: 115-47 (2007); Twyman, et al., *Expert Opin. Emerg. Drugs* 10: 185-218 (2005); Huang, et al., "ExpressTec: high level expression of biopharmaceuticals in cereal grains" in: K. J, (Ed.), *Modern Biopharmaceuticals*, Wiley VCH, 2005, pp. 931-47).

None of the aforementioned patents or publications discloses the production of non-glycosylated native transferrin protein in monocot seeds in high yield. It is desirable to provide for the production of non-glycosylated native transferrin protein in high yield free from contaminating source agents in order to provide a sufficient supply of transferrin in serum-free cell culture medium as well as in therapeutic compositions for the patient population with conditions treatable by administration of transferrin protein.

SUMMARY

Due to the high risk of contamination with blood-borne pathogens from the use of human- or animal plasma-derived transferrin, it is advantageous to produce recombinant transferrin from an alternative source, such as a crop plant, for use as a substitute for native human- or animal plasma-derived transferrin. Production of transferrin proteins in plants mitigates any possible contamination of the transferrin protein fraction by human or animal viruses and other disease causative agents found in human or animal plasma product fractions. In one aspect, the present disclosure provides expression of recombinant human transferrin (rhTF) in monocots, for example rice (*Oryza sativa* L.) grains, at high levels of expression, e.g., 1% seed dry weight (10 g/kg). The recombinant human transferrin was extracted with saline buffers and then purified by a one-step anion exchange chromatographic process to greater than 95% purity. The rice-derived recombinant human transferrin was biochemically and functionally characterized, and shown to be not only biochemically similar to the native human transferrin, but also functionally the same as native transferrin in terms of reversible iron binding and promoting cell growth and productivity. Specifically, the expressed rhTF was shown to be non-N-glycosylated by MALDI and PNGase F enzyme digestion analyses although the entire amino acid sequence of rhTF including its N-glycosylation sites had not been genetically modified to remove N-linked glycosylation sites. This monocot-derived rhTF was proved to be not only biochemically similar to the native hTF, but also functionally equivalent to the native hTF. Specifically, the monocot-derived rhTF reversibly bound iron and promoted cell growth and productivity. The ease of extraction and purification of recombinant hTF protein makes the present disclosure a viable system for commercial production of rhTF at high levels and low cost. Thus, the monocot-derived recombinant human transferrin described herein provides a safe and low cost alternative to human or animal plasma-derived transferrin for use in cell culture-based biopharmaceutical production of protein therapeutics and vaccines.

In one aspect, the disclosure provides a method of producing a recombinant non-glycosylated transferrin protein in monocot plant seeds, comprising the steps of:

(a) transforming a monocot plant cell with a chimeric gene comprising (i) a promoter from the gene of a seed maturation-specific monocot plant storage protein, (ii) a first DNA sequence, operably linked to said promoter, encoding a monocot plant seed-specific signal sequence capable of targeting a polypeptide linked thereto to a monocot plant seed endosperm cell, and (iii) a second DNA sequence, linked in translation frame with the first DNA sequence, encoding a natural transferrin protein, wherein the first DNA sequence and the second DNA sequence together encode a fusion protein comprising an N-terminal signal sequence and the tranferrin protein;

(b) growing monocot plant from the transformed monocot plant cell for a time sufficient to produce seeds containing the transferrin protein; and (c) harvesting the seeds from the plant, wherein the transferrin protein constitutes at least 0.1% seed weight of the harvested seeds.

In some embodiments, the transgenic monocot plant may further comprise a nucleic acid that encodes at least one transcription factor selected from the group consisting of O2 (encoded by the sequence set forth as SEQ ID NO: 20), PBF (encoded by the sequence set forth as SEQ ID NO: 21) and Reb (encoded by the sequence set forth as SEQ ID NO: 22).

The disclosure also provides a monocot plant seed-derived composition, selected from whole-seed food composition, a flour composition, an extract composition and a malt composition, prepared from the harvested seeds obtained by the disclosed method. In certain embodiments, the transferrin protein constitutes at least 1.0% of the dry weight the seed-derived composition.

The disclosure further provides a monocot seed-derived composition comprising an non-glycosylated transferrin protein, and at least one pharmaceutically acceptable excipient or nutrient, wherein the non-glycosylated transferrin protein is produced in a monocot plant containing a nucleic acid sequence encoding the transferrin protein and is extracted from seed harvested from the monocot plant. The excipient or nutrient is from a heterologous source other than the monocot plant. The formulation can be used for parenteral, enteric, inhalation, intranasal or topical delivery.

A serum-free cell culture medium comprising an extract of monocot seed expressing non-glycosylated transferrin protein and a method of making the serum-free cell culture medium are provided.

These and other objects and features of the claimed subject matter will become more fully apparent when the following detailed description is read in conjunction with the accompanying drawings and claims.

BRIEF DESCRIPTION OF THE FIGURES

FIG. 5 presents an SDS-PAGE analysis of different fractions upon purification of rice-derived rhTF protein extracts.

DETAILED DESCRIPTION

Figures 1, 2:
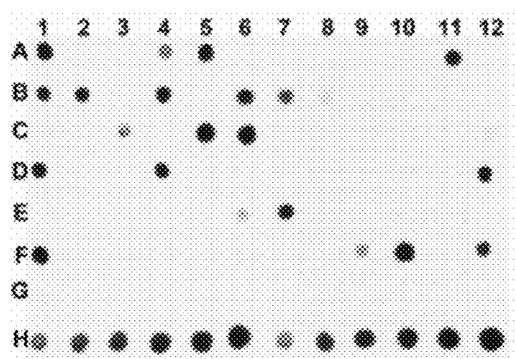
FIG. 1 provides a diagram of an exemplary construct for high level expression of transferrin in monocots.
FIG. 2 provides an immuno dot-blot expression analysis of transgenic rice seeds expressing hTF.

Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art.

7.1 Definitions

As used herein, the singular forms "a," "an," and "the" include plural referents unless the context clearly dictates otherwise. Thus, for example, reference to a "monocot plant" can mean, for example, a single monocot plant, such as a rice plant, or it can mean two or more of the same or different species of monocot plants.

As used herein, the following terms are intended to have the following meanings:

The term "stably transformed" with reference to a plant cell means the plant cell has a non-native (heterologous) nucleic acid sequence integrated into its genome which is maintained through two or more generations.

"Chimeric gene" or "heterologous nucleic acid construct," as defined herein refers to a construct which has been introduced into a host and may include parts of different genes of exogenous or autologous origin, including regulatory elements. A chimeric gene construct for plant/seed transformation is typically composed of a transcriptional regulatory region (promoter) operably linked to a heterologous protein coding sequence, or, in a selectable marker heterologous nucleic acid construct, to a selectable marker gene encoding a protein conferring antibiotic resistance to transformed plant cells. A typical chimeric gene of the present disclosure, includes a transcriptional regulatory region inducible during seed development, a protein coding sequence, and a terminator sequence. A chimeric gene construct may also include a second DNA sequence encoding a signal peptide if secretion of the target protein is desired.

The term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

The term "sequence identity" means nucleic acid or amino acid sequence identity in two or more aligned sequences, aligned using a sequence alignment program.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

The term "% homology" is used interchangeably herein with the term "% identity" and refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 70% sequence identity over a length of the given sequence. Exemplary levels of sequence identity include, but are not limited to 70%, 75% 80%, 85%, 90% or 95% or more sequence identity to a given sequence, e.g., the coding sequence for transferrin, as described herein.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See ncbi.nlm.gov/BLAST/. See, also, Altschul, S. F. et al., 1990 and Altschul, S. F. et al., 1997).

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook et al, 1989, Chapters 9 and 11, and in Ausubel et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

"Heterologous DNA" refers to DNA which has been introduced into plant cells from another source, or which can be from a plant source, including the same plant source, but which is under the control of a promoter that does not normally regulate expression of the heterologous DNA.

"Heterologous protein" is a protein encoded by a heterologous DNA.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

A plant cell, tissue, organ, or plant into which a heterologous nucleic acid construct comprising the coding sequence for an anti-microbial protein or peptide has been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of the coding sequence for an anti-microbial protein. Hence, a plant of the present disclosure will include any plant which has a cell containing introduced nucleic acid sequences, regardless of whether the sequence was introduced into the plant directly through transformation means or introduced by generational transfer from a progenitor cell which originally received the construct by direct transformation.

The term "transgenic plant" refers to a plant that has incorporated exogenous nucleic acid sequences, i.e., nucleic acid sequences which are not present in the native ("untransformed") plant or plant cell. Thus a plant having within its cells a heterologous polynucleotide is referred to herein as a "transgenic plant." The heterologous polynucleotide can be either stably integrated into the genome, or can be extra-chromosomal. The polynucleotide of the present disclosure may be stably integrated into the genome such that the polynucleotide is passed on to successive generations. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

The terms "transformed," "stably transformed" or "transgenic" with reference to a plant cell means the plant cell has a non-native (heterologous) nucleic acid sequence integrated into its genome which is maintained through two or more generations.

The term "expression" with respect to a protein or peptide refers to the process by which the protein or peptide is produced based on the nucleic acid sequence of a gene. The process includes both transcription and translation. The term "expression" may also be used with respect to the generation of RNA from a DNA sequence.

The term "introduced" in the context of inserting a nucleic acid sequence into a cell, means "transfection," or "transformation" or "transduction" and includes the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

By "host cell" is meant a cell containing a vector and supporting the replication and/or transcription and/or expression of the heterologous nucleic acid sequence.

A "plant cell" refers to any cell derived from a plant, including undifferentiated tissue (e.g., callus) as well as plant seeds, pollen, propagules, embryos, suspension cultures, meristematic regions, leaves, roots, shoots, gametophytes, sporophytes and microspores.

The term "mature plant" refers to a fully differentiated plant.

The term "seed product" includes, but is not limited to, seed fractions such as de-hulled whole seed, a flour composition (seed that has been de-hulled by milling and ground into a powder) a seed extract composition, in some embodiments, a protein extract (where the protein fraction of the flour has been separated from the carbohydrate fraction), a malt composition (including malt extract or malt syrup) and/or a purified protein fraction derived from the transgenic grain.

The term "biological activity" refers to any biological activity typically attributed to that protein by those of skill in the art.

The term "non-nutritional" refers to a pharmaceutically acceptable excipient which does not as its primary effect provide nutrition to the recipient. The excipient may provide one of the following services to an enterically delivered formulation, including acting as a carrier for a therapeutic protein, protecting the protein from acids in the digestive tract, providing a time-release of the active ingredients being delivered, or otherwise providing a useful quality to the formulation in order to administer to the patient the transferrin protein.

"Monocot seed components" refers to carbohydrate, protein, and lipid components extractable from monocot seeds, typically mature monocot seeds.

"Seed maturation" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

"Maturation-specific protein promoter" refers to a promoter exhibiting substantially upregulated activity (greater than 25%) during seed maturation.

A "signal sequence" is an N- or C-terminal polypeptide sequence which is effective to localize the peptide or protein to which it is attached to a selected intracellular or extracellular region. In some embodiments, the signal sequence targets the attached peptide or protein to a location such as an endosperm cell, in certain embodiments, an endosperm-cell organelle, such as an intracellular vacuole or other protein storage body, chloroplast, mitochondria, or endoplasmic reticulum, or extracellular space, following secretion from the host cell.

"Transferrin" can refer to a transferrin protein or protein-encoding sequence from an animal, such as a mammal, including a human. Exemplary amino acid sequences for mammalian transferrins are disclosed herein as the mature human transferrin protein Swiss-Prot accession number P02787, (identified herein as SEQ ID NO: 3); murine transferrin protein GenBank accession AAL34533.1 (identified herein as SEQ ID NO: 24); rat transferrin protein GenBank accession BAA07458.1 (identified herein as SEQ ID NO: 25); porcine transferrin protein GenBank accession CAQ34904.1 (identified herein as SEQ ID NO: 26); and macaque transferrin protein GenBank accession ACB11584.1 (identified herein as SEQ ID NO: 27).

"Non-glycosylated" or "unglycosylated" means without observable N-linked glycosylation, within the limits of detection by isoelectric focusing, PNGase F digestion and/or MALDI analysis. These terms make no reference to or implications about the O-linked glycosylation status of a protein.

"Native transferrin" means transferrin protein that is not produced from a mutated recombinant gene.

"Plant-derived" means that the source of the ingredient is a plant.

"Dry weight percent" or "% dry weight" or "percent seed dry weight" means, for example, a protein-yield of grams transferrin per kilogram of dry seeds. For example, 1% seed dry weight of rice-expressed transferrin means that 1 kilogram of rice grains yields 10 grams of transferrin protein.

"Total protein" and "total soluble protein" are used interchangeably, unless otherwise specified. Thus, unless otherwise noted, any given weight of total protein measured should be interpreted by the skilled artisan to mean total soluble protein. Further, a value given in μg/mg TSP to the corresponding value given in % TSP. As an example, 1 μg/1 mg TSP is equivalent to 1 μg per 1000 μg TSP (or 0.001 μg/μg TSP) which, expressed as a percentage of TSP in μg weight, would be 0.1% TSP measured in μg. For example, 30.3 μg/mg total (soluble) protein. This translates to 0.0303 μg per μg TSP, which, stated as a percentage, equals 3.03% TSP.

Units can also be expressed as μg per grain of monocot seed. This weight can be correlated with the percentage of total soluble protein, given that the average weight of a seed/grain and how much of this weight is represented by the TSP are matters readily known to skilled artisans. For example, the 1000 grain weight of rice is, on average, approximately 20-25 grams, which translates to 20-25 mg (or 20,000-25,000 μg) per rice grain. As one example, a transgenic rice plant may typically yield 190 μg total soluble protein per grain which is roughly equivalent to 0.8% grain weight (190 μg divided by 25,000 μg=0.0076 which is rounded up to 0.8%).

As is known in the art, "endosperm" or "endosperm tissue" is a seed storage tissue found in mature seeds.

The terms "crude extract," "partially-purified" or "substantially unpurified" means that a composition made from the transgenic monocot seed is not subjected to significant purification steps, such as chromatographic protein purification and fractionation steps.

1.2 Detailed Description

In some embodiments, the host cell is a monocot plant cell, such as, for example, a monocot endosperm cell. Other host cells may be used as secondary hosts, including bacterial, yeast, insect, amphibian or mammalian cells, to move DNA to a desired plant host cell.

The polynucleotides of the disclosure may be in the form of RNA or in the form of DNA, and include messenger RNA, synthetic RNA and DNA, cDNA, and genomic DNA The DNA may be double-stranded or single-stranded, and if single-stranded may be the coding strand or the non-coding (antisense, complementary) strand.

Expression vectors for use in the present disclosure are chimeric nucleic acid constructs (or expression vectors or cassettes), designed for operation in plants, with associated upstream and downstream sequences.

In general, expression vectors can include the following operably linked components that constitute a chimeric gene: a promoter from the gene of a maturation-specific monocot plant storage protein, a first DNA sequence, operably linked to the promoter, encoding a monocot plant seed-specific signal sequence (such as an N-terminal leader sequence or a C-terminal trailer sequence) capable of targeting a polypeptide linked thereto to an endosperm cell, in some embodiments an endosperm-cell organelle, such as a protein storage body, and a second DNA sequence, linked in translation frame with the first DNA sequence, encoding a transferrin protein. The signal sequence may be cleaved from the transferrin protein in the plant cell.

An exemplary DNA sequence encoding native human transferrin is set forth as SEQ ID NO: 1. An exemplary codon-optimized DNA sequence encoding human transferrin is set forth as SEQ ID NO: 2.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

Numerous types of appropriate expression vectors, and suitable regulatory sequences are known in the art for a variety of plant host cells. The promoter region is chosen to be regulated in a manner allowing for induction under seed-maturation conditions. In one aspect, the expression construct includes a promoter which exhibits specifically upregulated activity during seed maturation. Promoters are typically derived from cereals such as rice, barley, wheat, oat, rye, corn, millet, triticale or sorghum. Examples of such promoters include the maturation-specific promoter region associated with one of the following maturation-specific monocot plant storage proteins: rice glutelins, oryzins, and prolamines, barley hordeins, wheat gliadins and glutelins, maize zeins and glutelins, oat glutelins, and sorghum kafirins, millet pennisetins, and rye secalins. Exemplary regulatory regions from these genes are exemplified by SEQ ID NOS: 4-12. Some promoters suitable for expression in maturing seeds include the barley endosperm-specific B1-hordein promoter, GluB-2 promoter, Bx7 promoter, Gt3 promoter, GluB-1 promoter and Rp-6 promoter, particularly if these promoters are used in conjunction with transcription factors.

"Alpha-amylase" as used herein refers to an enzyme which principally breaks starch into dextrins. "Beta-amylase" as used herein refers to an enzyme which converts start and dextrins into maltose. An exemplary coding sequence of the rice alpha-amylase (RAmy3D) gene is set forth in GenBank accession M59351.1 (identified herein as SEQ ID NO: 28). See Huang, et al., *Nucleic Acids Res.* 18 (23), 7007-7014 (1990).

Of particular interest is the expression of the nucleic acid encoding a transferrin protein from a promoter that is preferentially expressed in plant seed tissue. Examples of such promoter sequences include those sequences derived from sequences encoding plant storage protein genes or from genes involved in fatty acid biosynthesis in oilseeds. Exemplary promoters include a glutelin (Gt1) promoter, which effects gene expression in the outer layer of the endosperm, and a globulin (Glb) promoter, which effects gene expression in the center of the endosperm. Promoter sequences for regulating transcription of gene coding sequences operably linked thereto include naturally-occurring promoters, or regions thereof capable of directing seed-specific transcription, and hybrid promoters, which combine elements of more than one promoter. Methods for construction such hybrid promoters are well known in the art.

In some cases, the promoter is native to the same plant species as the plant cells into which the chimeric nucleic acid construct is to be introduced. In other embodiments, the promoter is heterologous to the plant host cell.

Alternatively, a seed-specific promoter from one type of monocot may be used regulate transcription of a nucleic acid coding sequence from a different monocot or a non-cereal monocot.

In addition to encoding the protein of interest, the expression cassette or heterologous nucleic acid construct includes DNA encoding a signal peptide that allows processing and translocation of the protein, as appropriate. Exemplary signal sequences are those sequences associated with the monocot maturation-specific genes: glutelins, prolamines, hordeins, gliadins, glutenins, zeins, albumin, globulin, AOP glucose pyrophosphorylase, starch synthase, branching enzyme, Em, and lea. Exemplary sequences encoding a signal peptide for a protein storage body are identified herein as SEQ ID NOS: 13-19.

In one embodiment, the method is directed toward the localization of proteins in an endosperm cell, in some embodiments an endosperm-cell organelle, such as a protein storage body, mitochondrion, endoplasmic reticulum, vacuole, chloroplast or other plastidic compartment. For example, when proteins are targeted to plastids, such as chloroplasts, in order for expression to take place the construct also employs the use of sequences to direct the gene product to the plastid, Such sequences are referred to herein as chloroplast transit peptides (CTP) or plastid transit peptides (PTP). In this manner, when the gene of interest is not directly inserted into the plastid, the expression construct additionally contains a gene encoding a transit peptide to direct the gene of interest to the plastid. The chloroplast transit peptides may be derived from the gene of interest, or may be derived from a heterologous sequence having a CTP. Such transit peptides are known in the art. (See, for example, Von Heijne et al., 1991 *Plant Mol. Biol. Rep.,* 9:104-126; and U.S. Pat. Nos. 4,940,835 and 5,728,925). Additional transit peptides for the translocation of the protein to the endoplasmic reticulum (ER) (Chrispeels K., *Ann. Rev. Plant Phys. Plant Mol. Biol.,* 42:21-53, 1991), nuclear localization signals (Shieh et al., *Plant Physiol.* 1993 February; 101(2): 353-361; Varagona et al., *Plant Cell* 1992 October; 4(10): 1213-1227) or vacuole (Raikhel N., *Plant Phys.,* 100:1627-1632, 1992; and U.S. Pat. No. 5,360,726) may also find use in the constructs of the present disclosure.

Another exemplary class of signal/targeting/transport sequences are sequences effective to promote secretion of heterologous protein from aleurone cells during seed germination, including the signal sequences associated with alpha-amylase, protease, carboxypeptidase, endoprotease, ribonuclease, DNase/RNase, (1-3)-beta-glucanase, (1-3)(1-4)-beta-glucanase, esterase, acid phosphatase, pentosamine, endoxylanase, β-xylopyranosidase, arabinofuranosidase, beta-glucosidase, (1-6)-beta-glucanase, perioxidase, and lysophospholipase.

Since many protein storage proteins are under the control of a maturation-specific promoter, and this promoter is operably linked to a signal sequence for targeting to a protein body, the promoter and signal sequence can be isolated from a single protein-storage gene, then operably linked to a transferrin protein in the chimeric gene construction. One exemplary promoter-signal sequence combination is exemplified in the sequence identified by SEQ ID NO:4, in which the promoter and signal sequence both come from the rice Gt1 gene regulatory region. Alternatively, the promoter and leader sequence may be derived from different genes. One exemplary promoter-signal sequence combination is the rice Glb promoter linked to the rice Gt1 leader sequence (SEQ ID NO:5).

Expression vectors or heterologous nucleic acid constructs designed for operation in plants comprise companion sequences upstream and downstream to the expression cassette. The companion sequences are of plasmid or viral origin and provide necessary characteristics to the vector to permit the vector to move DNA from a secondary host to the plant host, such as, sequences containing an origin of replication and a selectable marker. Typical secondary hosts include bacteria and yeast.

In one embodiment, the secondary host is *E. coli*, the origin of replication is a ColE1-type, and the selectable marker is a gene encoding ampicillin resistance. Such sequences are well known in the art and are commercially available as well (e.g., Clontech, Palo Alto, Calif.; Stratagene, La Jolla, Calif.

The transcription termination region may be taken from a gene where it is normally associated with the transcriptional initiation region or may be taken from a different gene. Exemplary transcriptional termination regions include the NOS terminator from *Agrobacterium* Ti plasmid and the rice α-amylase terminator.

Polyadenylation tails may also be added to the expression cassette to optimize high levels of transcription and proper transcription termination, respectively. Polyadenylation sequences include, but are not limited to, the *Agrobacterium* octopine synthetase signal, or the nopaline synthase of the same species.

Suitable selectable markers for selection in plant cells include, but are not limited to, antibiotic resistance genes, such as, kanamycin (nptll), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed is one which allows for selection of transformed cells as compared to cells lacking the DNA which has been introduced. The selectable marker gene is one which facilitates selection at the tissue culture stage, e.g., a kanamyacin, hygromycin or ampicillin resistance gene.

The vectors of the present disclosure may also be modified to include intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors may comprise a disarmed plant tumor inducing plasmid of *Agrobacterium tumefaciens*.

In general, a selected nucleic acid sequence is inserted into an appropriate restriction endonuclease site or sites in the vector. Standard methods for cutting, ligating and transformation into a secondary host cell, known to those of skill in the art, are used in constructing vectors for use in the present disclosure. (See generally, Maniatis et al. *Molecular Cloning: A Laboratory Manual,* 2nd Edition, 1989; Ausubel et al. *Current Protocols in Molecular Biology*, John Wiley & Sons, New York, N.Y., 1993; and Gelvin et al., eds. *Plant Molecular Biology Manual,* 1990).

Plant cells or tissues are transformed with expression constructs (heterologous nucleic acid constructs, e.g., plasmid DNA into which the gene of interest has been inserted) using a variety of standard techniques. Effective introduction of vectors in order to facilitate enhanced plant gene expression is an important aspect of the disclosure. The vector sequences may be stably transformed, and may be integrated into the host genome.

The method used for transformation of host plant cells is not critical to the present disclosure. The skilled artisan will recognize that a wide variety of transformation techniques exist in the art, and new techniques are continually becoming available. Any technique that is suitable for the target host plant may be employed within the scope of the present disclosure. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, *Agrobacterium*-mediated transformation, liposome-mediated transformation, protoplast fusion or microprojectile bombardment (Christou, 1992; Sanford et al., 1993). The skilled artisan can refer to the literature for details and select suitable techniques for use in the presently disclosed.

When *Agrobacterium* is used for plant cell transformation, a vector is introduced into the *Agrobacterium* host for homologous recombination with T-DNA or the Ti- or Ri-plasmid present in the *Agrobacterium* host The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host The armed plasmid can give a mixture of normal plant cells and gall.

In some instances where *Agrobacterium* is used as the vehicle for transforming host plant cells, the expression or transcription construct bordered by the T-DNA border region(s) is inserted into a broad host range vector capable of replication in *E. coli* and *Agrobacterium*, examples of which are described in the literature, for example pRK2 or derivatives thereof. See, for example, Ditta et al., 1980 and EPA 0 120 515. Alternatively, one may insert the sequences to be expressed in plant cells into a vector containing separate replication sequences, one of which stabilizes the vector in *E. coli*, and the other in *Agrobacterium*. See, for example, McBride and Summerfeit 1990, wherein the pRiHRI (Jouanin, et al., 1985), origin of replication is utilized and provides for added stability of the plant expression vectors in host *Agrobacterium* cells.

Included with the expression construct and the T-DNA is one or more selectable marker coding sequences which allow for selection of transformed *Agrobacterium* and transformed plant cells. A number of antibiotic resistance markers have been developed for use with plant cells, these include genes inactivating antibiotics such as kanamycin, the aminoglycoside G418, hygromycin, or the like. The particular marker employed is not essential to this disclosure, with a particular marker preferred depending on the particular host and the manner of construction.

For *Agrobacterium*-mediated transformation of plant cells, explants are incubated with *Agrobacterium* for a time sufficient to result in infection, the bacteria killed, and the plant cells cultured in an appropriate selection medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of the recombinant protein produced by the plants.

There are a number of possible ways to obtain plant cells containing more than one expression construct. In one approach, plant cells are co-transformed with a first and second construct by inclusion of both expression constructs in a single transformation vector or by using separate vectors, one of which expresses desired genes. The second construct can be introduced into a plant that has already been transformed with the first expression construct, or alternatively, transformed plants, one having the first construct and one having the second construct, can be crossed to bring the constructs together in the same plant.

In one embodiment, the plants used in the methods of the present disclosure are derived from members of the taxonomic family known as the Gramineae. This includes all members of the grass family of which the edible varieties are known as cereals. The cereals include a wide variety of species such as wheat (*Triticum* sps.), rice (*Oryza* sps.) barley (*Hordeum* sps.) oats, (*Avena* sps.) rye (*Secale* sps.), corn (maize) (*Zea* sps.) and millet (*Pennisettum* sps.). In practicing the present disclosure, exemplary grains are rice, wheat, maize, barley, rye and triticale.

In order to produce transgenic plants that express transferrin protein in seeds, monocot plant cells or tissues derived from them are transformed with an expression vector comprising the coding sequence for a transferrin protein. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art Transgenic plant lines, e.g., rice, wheat, corn or barely, can be developed and genetic crosses carried out using conventional plant breeding techniques.

Transformed plant cells are screened for the ability to be cultured in selective media having a threshold concentration of a selective agent. Plant cells that grow on or in the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plant cells and regeneration of transgenic plants, which can produce a recombinant transferrin protein.

The expression of the recombinant transferrin protein may be confirmed using standard analytical techniques such as Western blot, ELISA, PCR, HPLC, NMR, or mass spectroscopy, together with assays for a biological activity specific to the particular protein being expressed.

A purified transferrin protein recombinantly produced in a plant cell, in some embodiments mostly free of contaminants of the host plant cell is also provided. In some embodiments, the presence or absence of plant glycosyl groups can indicate that the transferrin protein was produced in a plant, but does not significantly impair the biological activity of the transferrin protein in any of the applied therapeutic contexts (such that, for example, the recombinant TG has less than a 25% loss of activity or less than 10% loss of activity, as compared to a corresponding non-recombinant transferrin protein). Typically, in accordance with some embodiments, the transferrin protein constitutes at least about 0.1%, at least about 0.5%, at least about 1.0% or at least about 2.0% of the total soluble protein (TSP) in the seeds harvested from the transgenic plant. In some embodiments, however, protein expression is much higher than previously reported, i.e., at least about 3.0%, which makes commercial production quite feasible. Advantageously, protein expression is at least about 5.0%, at least about 10%, at least about 15%, at least about 20%, at least about 30%, or even at least about 40% of total soluble protein.

A plant seed product prepared from the harvested seeds is also provided in the present disclosure. Preferably, the transferrin protein constitutes at least about 3.0% of the total soluble protein in the seed product, more preferably at least about 5.0%, and most preferably at least about 10.0%. As shown in the figures, the expression of transferrin proteins in rice grains, represented by AAT, the three fibrinogen polypeptides and HSA represent at least about 10% of total soluble protein.

The present disclosure also provides compositions comprising transferrin proteins produced recombinantly in the seeds of monocot plants, and methods of making such compositions.

In practicing the disclosed method, a transferrin protein is produced in the seeds or grain of transgenic plants that express the nucleic acid coding sequence for the transferrin protein. After expression, the transferrin protein may be provided to a patient in substantially unpurified form (i.e., at least 10-20% of the composition comprises plant material), or the transferrin protein may be isolated or purified from a product of the mature seed (e.g., a flour, extract, malt or whole seed composition, etc.) and formulated for delivery to a patient.

Such compositions can comprise a formulation for the type of delivery intended. Delivery types can include, e.g. parenteral, enteric, inhalation, intranasal or topical delivery. Parenteral delivery can include, e.g. intravenous, intramuscular, or suppository. Enteric delivery can include, e.g. oral administration of a pill, capsule, or other formulation made with a non-nutritional pharmaceutically-acceptable excipient, or a composition with a nutrient from the transgenic plant, for example, in the grain extract in which the protein is made, or from a source other than the transgenic plant. Such nutrients include, for example, salts, saccharides, vitamins, minerals, amino acids, peptides, and proteins other than the transferrin protein. Intranasal and inhalant delivery systems can include spray or aerosol in the nostrils or mouth. Topical delivery can include, e.g. creams, topical sprays, or salves. Preferably, the composition is substantially free of contaminants of the transgenic plant, preferably containing less than 20% plant material, more preferably less than 10%, and most preferably, less than 5%. The preferable route of administration is enteric, and preferably the composition is non-nutritional.

The transferrin protein can be purified from the seed product by a mode including grinding, filtration, heat, pressure, salt extraction, evaporation, or chromatography.

The transferrin proteins produced in accordance with the disclosure also include all variants thereof, whether allelic variants or synthetic variants. A "variant" transferrin protein-encoding nucleic acid sequence may encode a variant transferrin protein amino acid sequence that is altered by one or more amino acids from the native transferrin protein sequence, preferably at least one amino acid substitution, deletion or insertion. The nucleic acid substitution, insertion or deletion leading to the variant may occur at any residue within the sequence, as long as the encoded amino acid sequence maintains substantially the same biological activity of the native transferrin protein. In another embodiment, the variant transferrin protein nucleic acid sequence may encode the same polypeptide as the native sequence but, due to the degeneracy of the genetic code, the variant has a nucleic acid sequence altered by one or more bases from the native polynucleotide sequence.

The variant nucleic acid sequence may encode a variant amino acid sequence that contains a "conservative" substitution, wherein the substituted amino acid has structural or chemical properties similar to the amino acid which it replaces and physicochemical amino acid side chain properties and high substitution frequencies in homologous proteins found in nature (as determined, e.g., by a standard Dayhoff frequency exchange matrix or BLOSUM matrix). In addition, or alternatively, the variant nucleic acid sequence may encode a variant amino acid sequence containing a "non-conservative" substitution, wherein the substituted amino acid has dissimilar structural or chemical properties to the amino acid it replaces. Standard substitution classes include six classes of amino acids based on common side chain properties and highest frequency of substitution in homologous proteins in nature, as is generally known to those of skill in the art and may be employed to develop variant transferrin protein-encoding nucleic acid sequences.

A transferrin protein-encoding nucleotide sequence may be engineered in order to alter the transferrin protein coding sequence for a variety of reasons, including but not limited to, alterations which modify the cloning, processing and/or expression of the transferrin protein by a cell.

As will be understood by those of skill in the art, in some cases it may be advantageous to use a transferrin protein-encoding nucleotide sequences possessing non-naturally occurring codons. Codons preferred by a particular eukaryotic host can be selected, for example, to increase the rate of transferrin protein expression or to produce recombinant RNA transcripts having desirable properties, such as a longer half-life, than transcripts produced from naturally occurring sequence. As an example, it has been shown that codons for genes expressed in rice are rich in guanine (G) or cytosine (C) in the third codon position (Huang et al., 1990). Changing low G+C content to a high G+C content has been found to increase the expression levels of foreign protein genes in barley grains (Horvath et al., 2000). The transferrin protein encoding genes can be synthesized by Operon Technologies (Alameda, Calif. based on the rice gene codon bias (Huang et al., 1990) along with the appropriate restriction sites for gene cloning. These 'codon-optimized' genes are then linked to regulatory/secretion sequences for seed-directed monocot expression and these chimeric genes then inserted into the appropriate plant transformation vectors.

Heterologous nucleic acid constructs may include the coding sequence for a transferrin protein (i) in isolation; (ii) in combination with additional coding sequences; such as fusion protein or signal peptide, in which the transferrin protein coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the transferrin protein coding sequence is a heterologous gene.

Depending upon the intended use, an expression construct may contain the nucleic acid sequence encoding the entire transferrin protein, or a portion thereof. For example, where transferrin protein sequences are used in constructs for use as a probe, it may be advantageous to prepare constructs containing only a particular portion of the transferrin protein encoding sequence, for example a sequence which is discovered to encode a highly conserved transferrin protein region.

In some embodiments, a seed composition containing a flour, extract, or malt obtained from mature monocot seeds and one or more seed-produced transferrin proteins in unpurified form is provided. Isolating the transferrin proteins from the flour can entail forming an extract composition by milling seeds to form a flour, extracting the flour with an aqueous buffered solution, and optionally, further treating the extract to partially concentrate the extract and/or remove unwanted components. In a preferred method, mature monocot seeds, such as rice seeds, are milled to a flour, and the flour then suspended in saline or in a buffer, such as Phosphate Buffered Saline ("PBS"), ammonium bicarbonate buffer, ammonium acetate buffer or Tris buffer. A volatile buffer or salt, such as ammonium bicarbonate or ammonium acetate may obviate the need for a salt-removing step, and thus simplify the extract processing method.

In some embodiments, the level of protein expressed in a transgenic plant is assessed from a crude extract or substantially unpurified composition from the plant seed. In some embodiments, a grain or milled grain or flour composition, an extract composition, or malt composition obtained from mature monocot seeds is produced in substantially unpurified form. The transferrin protein may be present in an amount between about 0.05 and 0.5 grams protein/kg total soluble protein. For a grain composition, the level of transferrin protein present may be between 0.1 to 1% of total seed weight. For an extract composition, the transferrin protein may be concentrated to form up to 5-40% or more of the total extract weight. A malt composition, which will contain a significant percent of malt sugars, in addition to native proteins as well as heterologous transferrin protein, will typically contain an amount of protein that is intermediate between that of grain and the extract.

The flour suspension is incubated with shaking for a period typically between 30 minutes and 4 hours, at a temperature between 20-55° C., The resulting homogenate is clarified either by filtration or centrifugation. The clarified filtrate or supernatant may be further processed, for example by ultrafiltration or dialysis or both to remove contaminants such as lipids, sugars and salt. Finally, the material may be dried, e.g., by lyophilization, to form a dry cake or powder. The extract combines advantages of high protein yields, essentially limiting losses associated with protein purification, In general, the protein once produced in a product of a mature seed can be further purified by standard methods known in the art, such as by filtration, affinity column, gel electrophoresis, and other such standard procedures. The purified protein can then be formulated as desired for delivery to a human patient. More than one protein can be combined for the therapeutic formulation. The protein may be purified and used in biomedical applications requiring a non-food administration of the protein.

Illustrative publications describing components of precursor compositions, as well as methods for preparing certain compositions include the following: U.S. patent Ser. Nos. 12/751,869 and 12/558,189; U.S. Patent Application Publication Nos. 20080318277; 20090156486; 20090258004; 20100031394 and 20030056244, and U.S. Pat. Nos. 6,991,824; 7,417,178 and 7,589,252 each of which is incorporated by reference herein in its entirety.

EXAMPLES

This section will describe the various different working examples that will be used to highlight features of the present disclosure. However, the present disclosure shall in no way be considered to be limited to the particular embodiments described below.

Example 1

Development of hTF Expression Vector and Plant Transformation

To obtain high level expression of rhTF in rice seeds, the mature hTF protein amino acid sequence (Swiss-Prot accession number P02787, set forth as SEQ ID NO: 3) was back translated into a nucleotide sequence with the codons optimized towards the codon-usage preference of rice genes (http://www.kazusa.or.jp/codon). At the same time, internal repeats and other features that might affect mRNA stability or translation efficiency were avoided. Compared to the native gene sequence for mature hTF, nucleotides in 339 out of a total of 679 codons were modified in the codon-optimized nucleotide sequence for hTF without altering the encoded amino acid sequence, and the G+C content was increased to 65% from 50.6% in the native hTF gene sequence. To facilitate the subcloning of hTF gene into an expression vector, the MO blunt-cutting restriction site that allows a cut right before the first nucleotide of the hTF gene was engineered, while two consecutive stop codons followed by an XhoI restriction site were engineered after the last genetic codon of hTF gene. The entire gene sequence was synthesized by the company DNA2.0 (Menlo Park, Calif.).

The synthesized nucleotide sequence for rhTF was digested with MlyI and XhoI, and ligated in frame into the NaeI-XhoI sites of the expression vector pAPI 405; and thereby the hTF gene is operably linked to the downstream of rice seed storage protein glutelin 1 gene promoter (Gt1) including its signal peptide encoding sequence (GenBank accession no. Y00687) and to the upstream of the nopaline synthase (nos) gene terminator of *Agrobacterium tumefaciens*. The resulting plasmid was validated by sequencing in both orientations, and designated as pVB24.

The plasmid pAPI146 was used to provide a selection marker in plant transformation. The pAPI146 consists of the hpt (hygromycin B phosphor-transferase) gene encoding the hygromycin B-resistant protein under the control of rice beta-glucanase 9 gene promoter, which restricts the expression of hpt gene only in rice calli (Huang, et al., *Plant Science* 161: 589-95 (2001)). The linear expression cassette DNA fragments comprising the region from promoter to terminator (without the superfluous backbone plasmid sequence) (See FIG. 1) in both pVB24 and pAPI146 plasmids were prepared by double digestion of EcoRI and HindIII, and used for transformation. Microprojectile bombardment-mediated transformation of embryonic calli induced from the mature seeds of two cultivars, Tapei309 and Bengal (*Oryza sativa L.* subsp. *Japonica*), was performed as described previously (Huang, et al., *Plant Science* 161: 589-95 (2001)). Before the regenerated transgenic seedlings were transferred to soil, PCR analysis of the plants were conducted with primers specific to the hTF gene using the Extract-N-Amp Plant PCR kit (Sigma, St. Louis, Mo.), and plants shown as negative were discarded. The regenerated transgenic plants are referred to as $R_0$ plants or transgenic events, and their progeny in successive generations are designated as $R_1$, $R_2$, etc.

To identify transgenic events expressing rhTF, pooled $R_1$ seeds of each transgenic event ($R_0$) were analyzed because of the genetic segregation of hemizygous hTF gene in the selfed $R_1$ seeds. Eight $R_1$ seeds from each transgenic event were randomly picked, dehusked, and placed into eight wells in the same column of a 96 deep-well plate. Five hundred microliters of PBS buffer (pH 7.4) and two 2 mm diameter steel beads were dispensed into each well. Then, a homogeneous extract was produced by agitating the plate with a Geno/Grinder 2000 (SPEX CertiPrep, Metuchen, N.J.) for 20 min at 1300 strokes/min followed by centrifugation with a microplate centrifuge at 4,000 rpm for 20 min. Equal amounts of supernatant extract from each seed of the same transgenic event were pooled. Two microliters of the pooled protein extracts from each transgenic event were spotted onto a nitrocellulose membrane. The blot was blocked in 5% non-fat milk in Tris buffered saline tween-20 (TBST) buffer for 1 h, and then incubated with rabbit anti-hTF antibody (Abeam, Cambridge, Mass.) in TBST buffer at a concentration of 1 μg/ml for 1 h followed by washing 4 times (5 min each) with TBST buffer. Then, the blots were incubated with 1:20,000 diluted anti-rabbit HRP (horseradish peroxidase)-conjugated antibody (BioRad, Hercules, Calif.) in TBST buffer for 1 h followed by 3 washes, 5 min each in TBST buffer, and one wash in TBS buffer for 5 min. The dot blots were then incubated with the enhanced chemiluminescence (ECL) reagent (Perice Biotechnology, Rockford, Ill.) for 5 min, and then exposed to X-ray film for signal detection. (See FIG. 2).

The seed protein extracts from positive transgenic plants identified by immuno-dot blot were resolved on a 4-20% Tris-glycine SDS-PAGE gel, electro-blotted onto a 0.45 um nitrocellulose membrane for 1 h at 100V in a Bio-Rad Protean System (BioRad, Hercules, Calif.). The subsequent western blot detection procedure was the same as described for dot-immunoblot except that the secondary antibody was the anti-rabbit alkaline phosphatase-conjugated antibody (BioRad, Hercules, Calif.) at a 1:4000 dilution and that the blot was developed with BCIP/NBT substrate (Sigma, St. Louis, Mo.).

Figure 3:
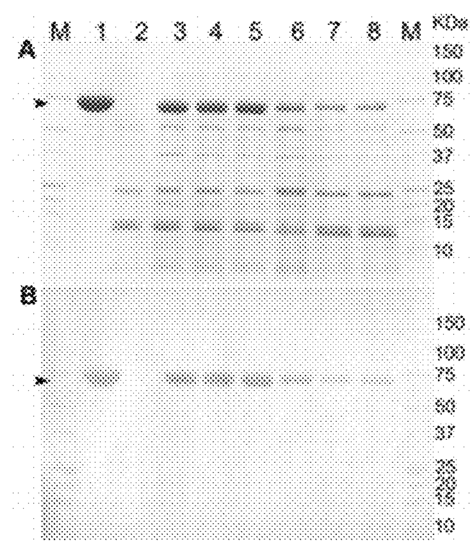
FIGS. 3A and 3B illustrate SDS-polyacrylamide gel electrophoresis (SDS-PAGE) and immunoblot analyses, respectively, of rhTF expressed in rice grain.

In total, 195 independent fertile transgenic rice plants ($R_0$) were generated from the particle bombardment transformation of two rice cultivars, Bengal and Taipei 309, by using linear rhTF gene expression cassette DNA (FIG. 1). The expression screening analysis of $R_1$ seeds through immuno dot-blot assay of protein extracts showed that 54 plants exhibited detectable expression of rhTF (FIG. 2). Rice seed TSP was extracted with 0.5 ml/seed of PBS buffer, pH 7.5 at room temperature for 1 h followed by centrifugation. 2 μl each of pooled protein extract from each transgenic event were spotted onto a nitrocellulose membrane. Spots in rows A to F and columns 1-12 are TSP extracts from 72 transgenic rice events. Spots G1-6 and G7-12 are TSP extracts from non-transgenic rice cultivars Bengal and Tapei309, respectively. Spots H1-6 are 10, 20, 50, 100, 200, and 500 ηg of nhTF (Sigma) spiked into 2 μl of Bengal seed protein extract, respectively. The spots H7-12 contained 10, 20, 50, 100, 200, and 500 ηg of nhTF (Sigma) spiked into 2 μl of Tapei309 seed protein extract, respectively. FIG. 3 shows SDS-PAGE and immunoblot analysis of rhTF expressed in rice grain. Total soluble protein TSP was extracted (but not concentrated, enriched or purified) from rice flour of transgenic lines expressing rhTF and non-transgenic line Bengal with 25 mM Tris-HCl, pH 7.5 at a 1:10 ratio (g/ml) of buffer to rice flour. TSP was directly loaded and resolved on two 4-20% Tris-glycine SDS-PAGE gels (Invitrogen). One gel was stained with Coomassie blue (FIG. 3A), and the other was used for western blot immunodetection with anti-hTF antibody (FIG. 3B). The arrowhead indicates the protein bands corresponding to rhTF. M=Molecular weight standard; lane 1=20 μg of nhTF (Sigma); lane 2=wild-type Bengal seed protein extract; lanes 3-8=transgenic events VB24-17, 54, 57, 401, 77, and 136, respectively. The SDS-PAGE analysis revealed a predominant protein band corresponding to the molecular weight of native hTF in positive transgenic seeds but not in the wild-type rice seeds (FIG. 3A), and the band was shown to specifically cross-react with anti-hTF antibody (FIG. 3B).

The transgenic events with high level expression of rhTF were identified through the denstometric analysis of the immuno dot signals followed by ELISA quantification. The expression level of rhTF in $R_1$ seeds was shown to be about 40% of total soluble protein (TSP). However, the measurement of rhTF expression level as a percent of TSP varied significantly depending on different extraction buffers and conditions used because the extracted amount of native rice seed proteins was significantly impacted by pH, ionic strength, and temperature (data not shown). Therefore, the percent of biomass dry weight represented by rhTF is a more reliable estimate of rhTF expression level. The expression level of rhTF in some selected transgenic events was up to 8.8 mg per gram (0.088%) of dry $R_1$ seed; and reached over 10 mg per gram (1%) of seed dry weight at $R_2$ generation and remained stable in subsequent generation (Table 1). The relatively lower expression level of rhTF in $R_1$ seeds compared to that in subsequent generation seeds is likely because of the poor plant growth performance and seed development of $R_0$ plants. Similar observations have been reported by others (Hood, et al., *Molecular Breeding* 3 (1997) 291-306; Chikwamba, et al., *Transgenic Research* 11 (2002) 479-493). Data are shown in Table 1, below.

TABLE 1

Quantification of rhTF expression levels over three generations in rice grains

| | VB24-17 | | VB24-54 | | VB24-57 | |
|---|---|---|---|---|---|---|
| Generation | n | Mean ± Std | n | Mean ± Std | n | Mean ± Std |
| $R_1^a$ | 8 | 8.8 ± 0.9 | 8 | 8.0 ± 0.8 | 8 | 7.7 ± 0.3 |
| $R_2^b$ | 59 | 10.2 ± 1.7 | 64 | 10.0 ± 1.7 | 76 | 10.1 ± 2.1 |
| $R_3^c$ | 10 | 10.5 ± 1.8 | 10 | 10.5 ± 1.4 | 15 | 10.1 ± 1.6 |

[a]Eight $R_1$ positive seeds from each transgenic event were assayed
[b]One gram of pooled $R_2$ seeds from a single TF-positive $R_1$ plant was assayed
[c]One gram of pooled $R_3$ seeds from each single homozygous $R_2$ plant was assayed Quantification of rhTF was performed by ELISA (enzyme-linked immunosorbent assay) with a hTF ELISA assay kit (Bethyl Labs, Montgomery, Tex.) by following the manufacturer's instructions, except that the purified hTF from Sigma was used to produce the standard curve. Low expression yield of recombinant proteins has been identified as one of the major limitations of plant expression systems (Lienard, et al., *Biotechnol. Annu. Rev.* 13 (2007) 115-47; Fischer, et al., *Curr. Opin. Plant Biol.* 7 (2004) 152-8), and Farran et al. (2002) suggested that the critical limit of plant-derived recombinant protein expression level for commercial viability is 0.01% mass weight (Farran, et al., *Transgenic Res.* 11 (2002) 337-46). The rice-derived rhTF expression level was 100 fold higher than this suggested critical limit. This extremely high expression level will contribute to significantly reduce the production cost, and will also benefit the downstream purification.

Figure 4:
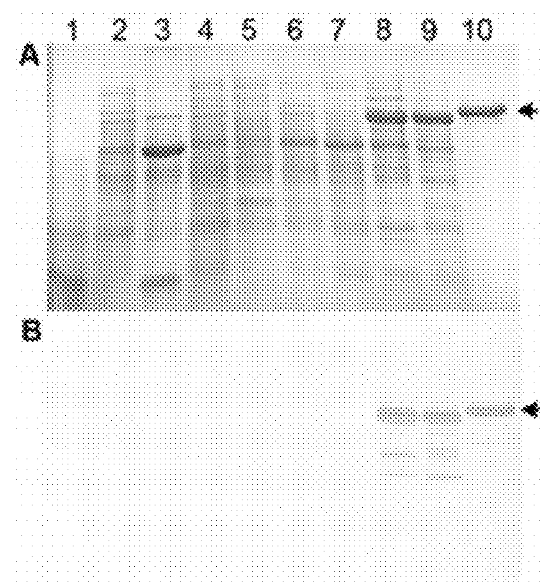
FIGS. 4A and 4B illustrate SDS-PAGE and immunoblot analyses, respectively, of tissue specific expression of rhTF in rice plant roots, stems, leaves, leaf sheaths, anthers with pollens, grain husks, pistils, immature seeds, and mature seeds.

To investigate the tissue-specificity of rhTF expression in rice, proteins were extracted from roots, stems, leaves, leaf sheaths, anthers with pollens, grain husks, pistils, immature seeds, and mature seeds, respectively, with PBS buffer (pH 7.4), resolved on two 4-20% Tris-glycine SDS-PAGE gels (Invitrogen), run simultaneously, and stained with LabSafe Gel Blue (G Biosciences) (FIG. 4A), or transferred to a membrane for immunodetection using anti-hTF antibody (FIG. 4B) as described above. Lanes 1-9=10 μg per lane crude protein extract from roots, stems, leaves, leaf sheaths, anthers with pollens, grain husks, pistils, immature seeds, and mature seeds, respectively. Lane 10=4 μg of commercial native hTF (Sigma), indicated by arrowhead. The analysis of the tissue specificity of rhTF expression demonstrated that the rhTF was expressed only in the maturing and mature seeds, but not in the root, stem, leaf, leaf sheath, grain husk, anther including pollen, and the pistils (FIG. 4). This is consistent with previous finding that the Gt1 gene promoter is developmentally regulated and active only in maturing rice seeds (Okita, et al., *J. Biol. Chem.* 264 (1989) 12573-81; Qu le, et al., *Plant Biotechnol. J.* 2 (2004) 113-25).

Example 3

Extraction and Purification of rhTF

Identification of the optimal extraction conditions for rhTF is important for developing a purification procedure that allows maximal protein purity and minimal purification costs. To find the optimal extraction condition for rhTF, the effect of temperature, buffer pH, ionic strength, and mixing time on protein extraction was investigated using 100 mg of rice seed flour in each treatment. The temperature effect on rhTF extraction was examined by extracting 100 mg of rice seed flour in 1 ml of PBS buffer, pH 7.4 at room temperature (RT), 37° C., 40° C., or 60° C., for 1 h. The effect of buffer pH on rhTF extractability was tested in a range from 4.5 to 10.0. The rice seed flour was extracted in each Eppendorf tube with 1 ml of 25 mM sodium acetate at pH 4.5, 5.0, 6.0; 25 mM Tris-HCl at pH 7.0, 7.5, 8.0, 9.0; or 25 mM CAPS, pH 10.0 for 1 h at RT. The ionic strength effect on rhTF extraction was determined by extracting 100 mg of rice flour in each of 1 ml 25 mM Tris-HCl, pH 8.0 with 100, 200, or 500 mM sodium chloride for 1 h at RT. The time effect on rhTF extraction was determined by extracting 100 mg of rice flour in 1 ml of 25 mM Tris-HCl, pH 8.0 for 10, 30, 60, or 120 min. After extraction, all samples were centrifuged at 13,000×g for 20 min, and the supernatants were assayed to estimate the total soluble protein (TSP) and rhTF protein content.

It was shown that while the amount of TSP increased with the increase in pH, the extracted rhTF protein was shown to increase with increase in pH from 4.5 to 7.0 but no substantial difference in the pH range of 7.0 to 10.0 (data not presented). Comparison of the effect of extraction time showed that 30 min extraction was already able to exact the maximum amount of rhTF. Neither the salt concentration nor the extraction temperature showed a significant effect on the rhTF extractability (data not shown). These results indicated that extraction of rhTF from rice flour with 25 mM Tris-HCl, pH 7.5 for 30 min at RT was the optimal condition to maximize the extraction of rhTF while minimizing the extraction of rice native proteins.

To develop a cost-effective procedure for purification of rhTF, different chromatography media and conditions were tested. The purification of rhTF protein was tested with hydrophobic interaction chromatography (HIC) medium Phenyl Sepharose 6 FF, anion exchange chromatography media Q (quaternary amine) and DEAE (diethyl amino ethane) Sepharose FF (GE, Piscataway, N.J.), respectively, using the Biologic LP chromatography system (Bio-Rad, Hercules, Calif.). Each type of chromatography media was packed to 5 cm high in a 1×10 cm Bio-Rad Econo column. The purification of rhTF protein using Phenyl Sepharose resin was carried out essentially as described in (Ali, et al., *Biochem. J.* 319 (Pt 1): 191-5 (1996)). For the purification of rhTF protein with anion exchange chromatography, the seed crude total proteins were extracted with 25 mM Tris-HCl buffer, pH 7.5 at a ratio of 1 to 10 of flour to buffer (g/ml) for 30 min at RT followed by centrifugation at 15,000×g for 30 min. The supernatant was filtered through a 0.2 um filter, and then loaded onto a DEAE or Q Sepharose column pre-equilibrated with 25 mM Tris-HCl buffer, pH 7.5. After the column was washed with 25 mM Tris-HCl buffer, pH 7.5 to the UV and conductivity baseline, the rhTF protein was eluted either by linear gradient from 0 to 100 mM NaCl in 25 mM Tris-HCl buffer, pH 7.5 or by a step elution with 40 mM NaCl in 25 mM Tris-HCl buffer, pH 7.5.

The HIC column with a Phenyl Sepharose was shown to be able to purify rhTF at a purity of 90%. However, a step of precipitating impure proteins with ammonium sulphate before loading onto the column could reduce the yield of rhTF and also add the purification cost. The weak anion exchange chromatography DEAE showed that the rhTF bound to the DEAE resin in the extraction buffer 25 mM Tris-HCl, pH 7.5 without the need of buffer exchange, while some rice proteins leaked out of the resin into the flow-through fractions during loading and washing. The rhTF could then be eluted from the DEAE resin with 40 mM NaCl in 25 mM Tris-HCl, pH 7.5, and was at a purity of greater than 95% based on the SDS-PAGE (FIG. 5). The purification of rhTF with the strong anion exchange chromatography Q Sepharose resin showed a very similar chromatographic profile to that of DEAE Sepharose column. However, the Q Sepharose resin bound rhTF protein more strongly than DEAE Sepharose resin, and the rhTF protein needed to be eluted with higher concentration of salts, resulting in coeluting more rice proteins. With the DEAE chromatography, we purified rhTF with four batches of 100 g seed flour and each batch consistently yielded the recovery rate of rhTF to 60%. These results showed that a one-column DEAE chromatography method can effectively purify rhTF from rice grain protein extracts. The ease of purifying rhTF with a single purification step is presumably enabled by both the high expression level of rhTF and the relatively simple protein composition in rice grain (Stoger, et al., *Plant Mol. Biol.* 42 (2000) 583-90), because either of them will lead to a higher enrichment of target protein in the starting material for purification, which can help simplify the purification process and reduce the cost. The ease and low cost of purification of recombinant proteins from rice grains have also been shown in our prior work with recombinant lactoferrin (Nandi, et al., *Transgenic Res.* 14 (2005) 237-49) and lysozyme (Huang, et al., *Molecular Breeding* 10 (2002) 83-94; Wilken, et al. *Biotechnol. Prog.* 22 (2006) 745-752).

Example 4

Amino-Terminal Sequence Analysis

Amino (N)-Terminal Sequence Analysis

Since a rice seed storage protein signal sequence targeting to the protein body in endosperm was fused to the N-terminus of the rhTF, N-terminal sequencing of rhTF was carried out to examine whether the rice signal sequence was cleaved correctly. Eleven sequencer cycles were analyzed, and the N-terminal sequence of rhTF was revealed as V-P-D-K-T-V-R-W-$X^c$-A-V (SEQ ID NO: 23), which is identical to nhTF except that the expected cysteine amino acid residue at cycle 9 was not determined. The undetected cysteine is expected because cysteine, without special modification, cannot be detected by N-terminal sequencing. This result indicates that the rice signal sequence before the mature rhTF protein was correctly removed at the expected position.

The purified rhTF was resolved on a 4-20% Tris-glycine SDS-PAGE gel (Invitrogen, Carlsbad, Calif.) and electroblotted onto a PVDF membrane (Bio-Rad, Hercules, Calif.) in 50 mM CAPS buffer, pH 10.0. The blot was stained with 0.1% Ponceau S in 0.1% acetic acid for 5 min, and destained in 0.1% acetic acid and ddH2O. The protein band corresponding to rhTF was excised and sequenced on an ABI 494-HT Procise Edman Sequencer at the Molecular Structure Facility at the University of California, Davis, Calif., US.

Example 5

MALDI (Matrix-Assisted Laser Desorption Ionization) Analysis of rhTF

Molecular Weight of rhTF

The MALDI analysis was carried out to estimate the molecular weight of rice-derived rhTF. Three sources of TFs, rice-derived rhTF, yeast-derived aglycosylated rhTF (Millipore, Billerica, Mass.), and native hTF (Sigma, St. Louis, Mo.), were all dialyzed against 50 mM sodium acetate, 5 mM EDTA, pH 4.9 overnight followed by dialyses in $ddH_2O$ to deplete iron that was bound to TFs. These iron-free or apo-TFs were further desalted using ZipTip™μ-C18 pipette tips (Millipore, Billerica, Mass.), eluted with a solution of 70% acetonitrile (ACN), 0.2% formic acid, and 5 mg/ml MALDI matrix (α-cyano-4-hydroxycinnamic acid), and spotted onto the MALDI target and analyzed with an Applied Biosystems 4700 Proteomics Analyzer (Applied Biosystems Inc., Foster City, Calif.) at the Molecular Structure Facility at the University of California, Davis, Calif., US.

Figure 6:
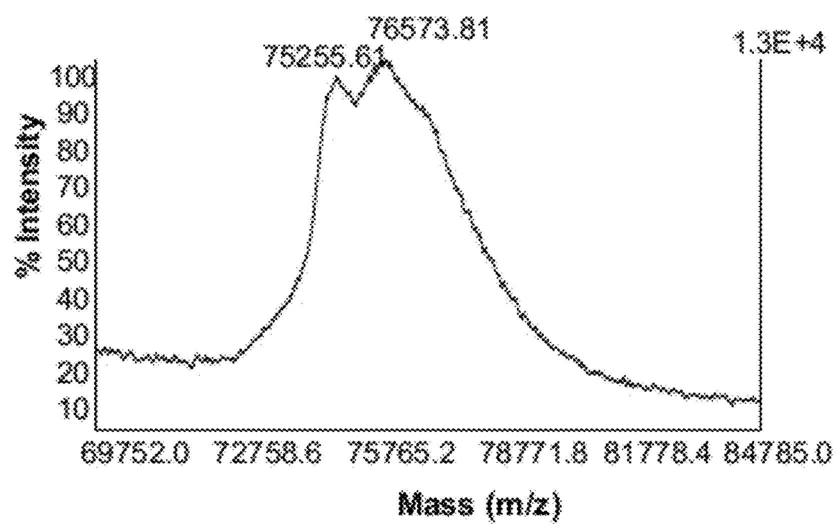
FIG. 6 presents a MALDI mass spectrum molecular weight analysis of purified rice-derived rhTF.

A close-up view of the MALDI spectrum of rhTF revealed a peak comprising two small split peaks on top with molecular weights of 75,255.6 and 76,573.8 Da, respectively (FIG. 6). This MALDI spectrum is similar to that of the yeast-derived aglycosylated rhTF but different from the N-glycosylated nhTF spectrum, which showed a single peak of 80,000 Da mass (Data not shown). The mass for the first split small peak of the rice-derived rhTF is close to the calculated mass of non-N-glycosylated nhTF (75,181.4 Da) with a mass shift of just 74.2 Da, and the mass for the second split small peak showed a mass increase of 1,392.4 Da. The size discrepancy between rhTF and N-glycosyalted nhTF as revealed by MALDI is consistent with the finding as shown in the SDS-PAGE gel analysis of rhTF (FIG. 5). Furthermore, the rice-derived rhTF molecular weight as revealed by MALDI is similar with that of the yeast-derived aglycosylated rhTF, suggesting that the rice-derived rhTF may not be N-glycosylated.

Example 6

PNGase F Digestion of rhTF

Glycosylation Modifications

Figure 7:
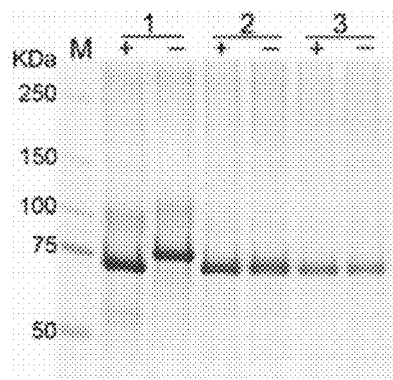
FIG. 7 presents a glycosylation state analysis by PNGase F treatment of rice-derived rhTF.

To evaluate the glycosylation status of rice-derived rhTF, the purified rhTF protein was subjected to digestion with peptide-N-glycosidase F (PNGase F) (Sigma, St. Louis, Mo.). The yeast-derived aglycosylated rhTF (Millipore, Billerica, Mass.) and native hTF (Sigma, St. Louis, Mo.) were also included for comparison (FIG. 7). The native hTF contains two N-glycosylation sites (N413 and N611Q) (MacGillivray, et al., *J. Biol. Chem.* 258 (1983) 3543-53), whereas the yeast-derived aglycosylated rhTF has two mutations of its N-glycosylation sites (N413Q and N611Q), rendering a protein without N-glycosylation (Sargent, et al., *BioMetals* (2006) 19:513-519).

All TFs were desalted and buffer exchanged into 20 mM ammonium bicarbonate, pH 8.6 using 10 KDa MWCO Microcon spin columns (Millipore, Billerica, Mass.) with a final TF concentration of 0.5 mg/ml. Then, 45 μl of each type of TF was aliquoted into an Eppendorf tube followed by adding 5 μl of 10× denaturant (0.2% SDS, 10 mM 2-mercaptoethanol, 20 mM ammonium bicarbonate, pH 8.6) and boiling for 10 min. After the samples were cooled to RT, 5 μl of 15% Triton X-100 was added followed by the addition of 5 μl (2.5 units) PNGase F to remove the glycans from TFs. The reaction was carried out at 37° C. overnight (16 h) and analyzed by resolving 15 μl of each reaction on 4-20% Tris-glycine SDS-PAGE gel (Invitrogen, Carlsbad, Calif.) and staining with LabSafe Gel Blue (G Biosciences, St. Louis, Mo.).

As expected, the N-glycosylated nhTF showed a clear downward shift in electrophoretic mobility after PNGase F treatment, and the yeast-derived aglycosylated rhTF showed no change before and after the PNGase F treatment. Surprisingly, the electrophoretic mobility of rice-derived rhTF also remained unchanged before and after the PNGase F treatment, and its molecular size was the same as that of deglycoslated native hTF by PNGase F and yeast-derived aglycosylated rhTF. This result is consistent with the data revealed by MALDI analysis, and they all suggest that rice-derived rhTF is not N-glycosylated. The absence of N-glycosylation in rice-derived rhTF is, however, inconsistent with our prior finding in recombinant human lactoferrin (a close relative to hTF), which is expressed in rice grain using the same expression vector for rhTF and shown to be N-glycosylated (Nandi, et al., *Transgenic Res.* 14 (2005) 237-49; Nandi, et al., *Plant Science* 163 (2002) 713-22). The mechanism of the formation of non-N-glycosylated rhTF warrants further investigation.

Example 7

Analysis of the Isoelectric Point of rhTF

The isoelectric point of rice-derived apo-rhTF was determined with a pre-cast Novex IEF (isoelectric focusing) gel, pH 3-10 (Invitrogen, Carlsbad, Calif.) according to manufacturer's instruction. Four micrograms of TF in dH2O were resolved at 100 V for 1 h, 200 V for 1 h, and 300 V for 30 min. The native apo-hTF (Sigma, St. Louis, Mo.) and the yeast-derived aglycosylated apo-rhTF (Millipore, Billerica, Mass.) were also loaded on the gel for comparison. Lane 1=native hTF (Sigma); lane 2=yeast-derived aglycosylated rhF (Millipore); lane 3=rice-derived rhTF. The gel was then fixed in 136 mM sulphosalicylic acid and 11.5% trichloroacetic acid (TCA) for 30 min and then stained in 0.1% Coomassie Brilliant Blue R-250 followed by destaining.

Figure 8:
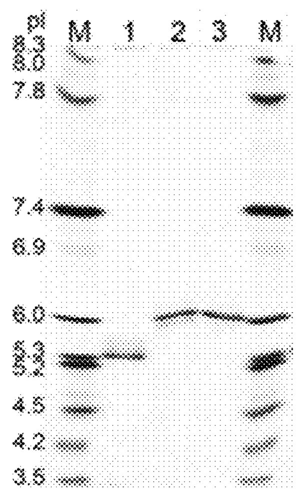
FIG. 8 presents an isoelectic focusing gel analysis of rice-derived rhTF.

The isoelectric point (pI) of rice-derived rhTF was shown to be 6.3, which is same as the pI of yeast-derived aglycosylated rhTF but one unit higher than the pI of the native hTF (5.3) (FIG. 8). The pI discrepancy of rhTF and native hTF is due to the negatively charged sialic acid residues present in the native hTF but absent in both rice-derived and yeast-derived rhTFs. The native hTF has two N-linked oligosaccharide chains, and each chain terminates in two or three antennae, each with terminal sialic acid residues (MacGillivray, et al., *J. Biol. Chem.* 258 (1983) 3543-53; Fu, et al., *Anal. Biochem.* 206 (1992) 53-63). It has been reported that loss of the sialic acid residues leads to a cathodic shift of the pI of TF molecules (Hoelkens, et al., *Glycoconj. J.* 14 (1997) 289-95). The yeast-derived aglycosylated rhTF has no N-linked glycans and sialic acid residues. The rhTF expressed in rice grain is not expected to have sialic acids either, as plants are presumably not capable of synthesizing sialic acids or at best just contain negligible amounts (Castilho, et al., *Plant Physiol.* 147 (2008) 331-9; Zeleny, et al., *Planta* 224 (2006) 222-7).

Example 8

RP-HPLC Analysis of rhTF

Conformation of rhTF The conformation and integrity of rice-derived apo-rhTF was assessed by comparing with the apo-nhTF using reverse phase liquid chromatography (RP-HPLC).

Both native apo-hTF (Sigma, St. Louis, Mo.) and rice-derived apo-rhTF were prepared in buffer A containing 0.1% trifluoroacetic acid (TFA) and 5% ACN at a concentration of 50 μg/ml and filtered through a 0.2 um syringe filter (PALL, Port Wash., N.Y.). Then 2.5 μg of each protein sample was injected to a pre-equilibrated Zorbax 3000SB-C8 column (Aglient, Santa Clara, Calif.) with buffer A using a Beckman Coulter System Gold 126 solvent module (Beckman, Fullerton, Calif.). The column was washed with three column volume of buffer A, and then run with a gradient from buffer A to 100% buffer B containing 0.04% TFA and 95% ACN in 12 column volume.

Figure 9:
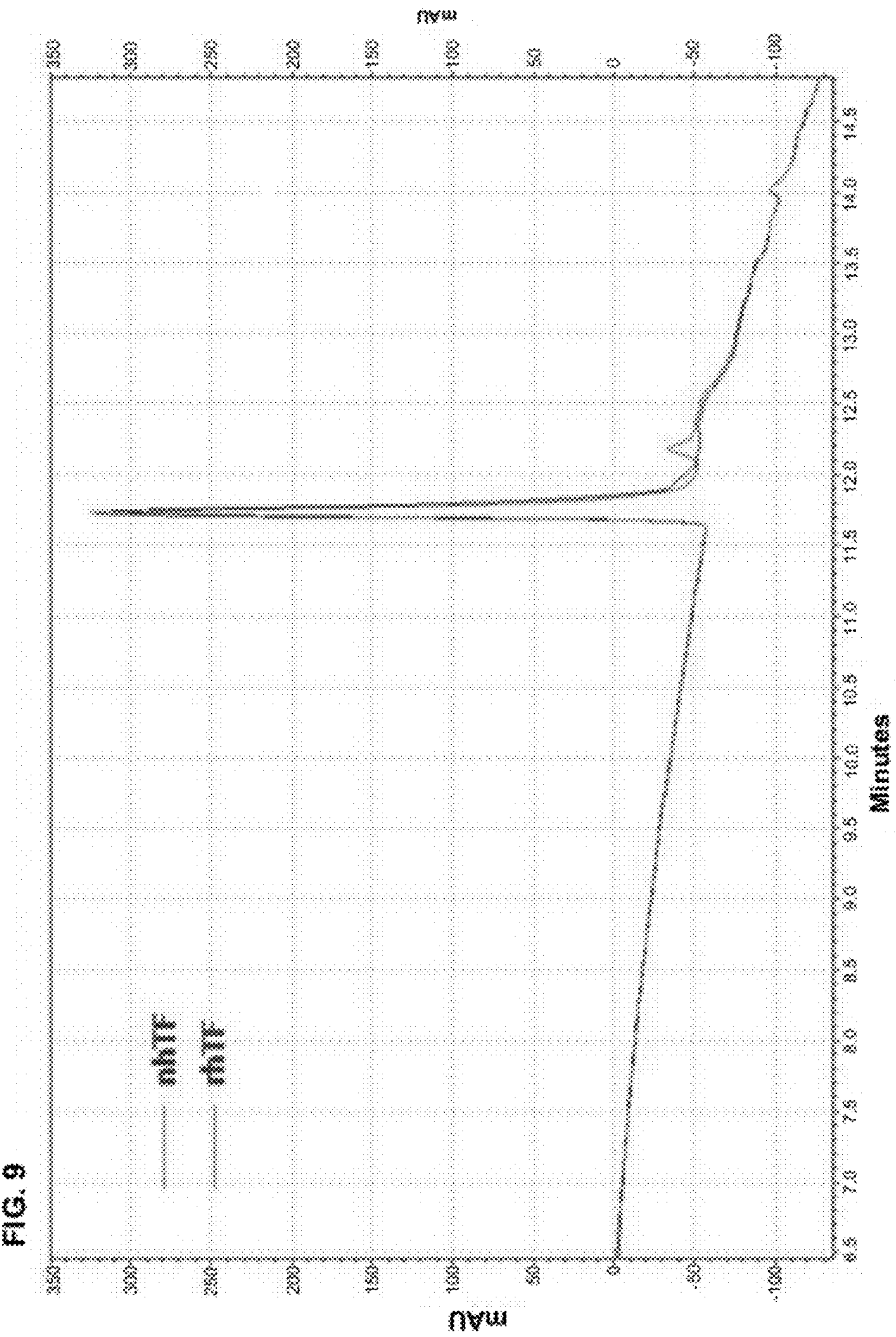
FIG. 9 provides a RP-HPLC comparison of rice-derived rhTF and native hTF ("nhTF").

RP-HPLC resolved both the rhTF and nhTF into a major peak corresponding to their respective monomer form of the molecule, and the two peaks were shown to have the same retention time (FIG. 9), suggesting that rice-derived rhTF has similar conformational structure as nhTF.

Example 9

Iron-Binding Assay of rhTF

To test the reversible iron binding capacity of rice-derived rhTF, the purified rhTF was first dialyzed against 50 mM sodium acetate, 5 mM EDTA, pH 4.9 overnight followed by sequential dialyses in ddH2O and 25 mM Tris-HCl, pH 7.5 to remove the iron that was bound to rhTF. Then, the apo-rhTF at a concentration of 5 mg/ml in 25 mM Tris-HCl buffer, pH 7.4+10 mM NaHCO3 was titrated with increasing amount of iron (III)-nitrilotriacetate (Fe3+-NTA). The spectra were scanned from 700 to 380 nm after each addition of Fe3+-NTA, and the reading was corrected for dilution. The iron-saturated rhTF was dialyzed in 25 mM Tris-HCl buffer, pH7.5 overnight with three buffer changes to remove the unbound iron, resulting in the holo-rhTF. The iron-binding status of rhTF with different iron saturation levels was assayed by examining the mobility of rhTF on the Urea-PAGE gel with the method as described in (Evans, et al., *Biochem. J.* 189: 541-46 (1980); Makey, et al., *Biochim. Biophys. Acta* 453 250-6 (1976)). Approximately 2 μg of each TF sample was mixed with equal volume of 2× sample buffer (89 mM Tris-borate, pH 8.4, 7 M urea, 50% sucrose, 0.01% bromophenol blue), loaded onto a Novex precast 6% TBE-Urea PAGE gel (7M urea), and electrophoresed in a buffer containing 89 mM Tris-borate, 20 mM EDTA, pH 8.4 for 2 h at 170 V. The gel was stained with Coomassie blue.

Results of Iron Binding Assay

Figure 10A:
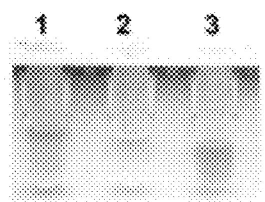
FIGS. 10A-D provide an analysis of iron-binding properties of rice-derived rhTF.
Figure 10C:
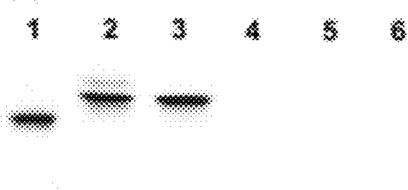
Figure 10B:
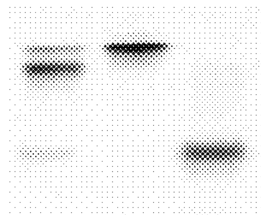
Figure 10D:
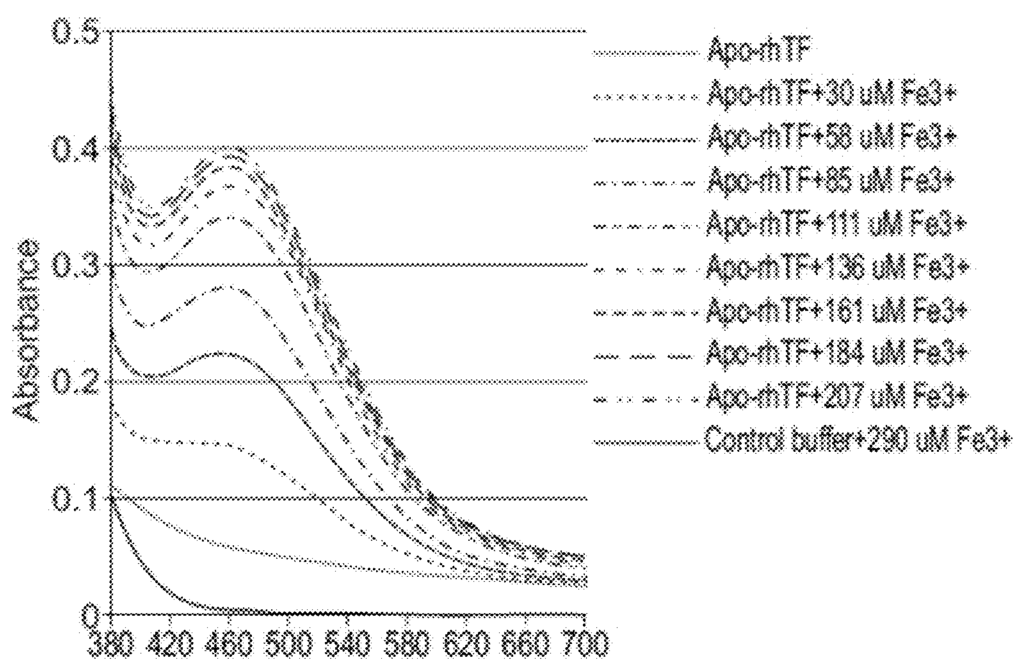

The biological function of TF was measured by assessing its ability to bind and release iron reversibly. The purified partially iron saturated (pis) rhTF from rice grains showed a salmon-pink color, a characteristic color of iron-bound TF, suggesting that rhTF has already bound iron in rice grains. After being dialyzed against 50 mM sodium acetate, 5 mM EDTA, pH 4.9 overnight followed by sequential dialysis in $ddH_2O$ and 25 mM Tris-HCl, pH 7.5, the pinkish rhTF became colorless (FIG. 10A), an indication of iron release from the pis-rhTF, resulting in the conversion into apo-rhTF. Apo-rhTF was titrated with increasing amounts of iron (III)-nitrilotriacetate ($Fe^{3+}$-NTA), and the visible spectra were scanned from 700 to 380 nm after each addition of $Fe^{3+}$-NTA and the reading corrected for dilution. Spectrophotometric titration of this apo-rhTF with iron ($Fe^{3+}$-NTA) showed a broad peak in the region of 465 to 470 nm, and the peak grew in size as the rhTF was gradually saturated with the increasing increments of iron (FIG. 10D D). At the same time, the pink color also gradually showed up in the titrated rhTF solution and became darker when rhTF was saturated with iron (FIG. 10A). The saturation of apo-rhTF with iron resulted in the production of holo-rhTF.

To evaluate the iron binding status of purified pis-rhTF and its derived apo- and holo-isoforms after iron depletion and saturation, these rhTF samples were subjected to a urea-PAGE gel electrophoresis analysis. The apo- and holo-rhTF both showed a single band but with slower and faster electrophoretic mobility, respectively, in the urea-PAGE gel (FIG. 10B). The slower and faster migrating forms of rhTF reflected the conformational change of rhTF without or with bound iron (Sargent, et al., *BioMetals* (2006) 19:513-519); Evans, et al., *Biochem. J.* 189 (1980) 541-46). The pis-rhTF showed three bands in the urea-PAGE gel; the slowest and the fastest bands corresponded to the apo- and holo-forms of rhTF, respectively, whereas the middle band represented the monoferric form of rhTF. The coexistence of apo-, holo- and monoferric-rhTF in the purified rhTF indicated that rhTF had been indeed partially saturated with iron in the rice grain. The monoferric form of rhTF was further inferred to have an iron bound in C-lobe of rhTF because the band was shown to be closer to the apo-rhTF, which is a characteristic of C-terminal monoferric TF (Evans, et al., *Biochem. J.* 189 (1980) 541-46; Mason, et al., *Protein Expr. Purif.* 36 (2004) 318-26). In normal serum with an iron concentration insufficient to saturate TF, the two monoferric forms of hTF (C- and N-terminal) can be revealed in the urea-PAGE gel because both N- and C-terminal iron-binding sites are occupied with iron although the N-terminal site is normally preferentially occupied (Zak, et al., *Blood* 68 (1986) 157-61; Williams, et al., *Biochem. J.* 185 (1980) 483-488). However, when the serum is dialyzed against a buffer at pH 7.4, iron is found to preferentially bind to the C-terminal site so that the N-terminal monoferric TF is undetectable in the urea-PAGE gel (Williams, et al., *Biochem. J.* 185 (1980) 483-488). Similarly, the rice-derived rhTF was extracted and purified at pH 7.5 followed by a step of dialysis at pH 7.5 to concentrate, and thus these conditions could cause the C-terminal iron-binding site of rhTF to be predominantly occupied with iron, resulting in the absence of the band corresponding to N-terminal monoferric rhTF.

The electrophoretic mobility of rice-derived apo- and holo-rhTF in urea-PAGE gel was compared to that of native hTF and the yeast-derived aglycosylated rhTF (FIG. 10. C; lane 1=native apo-hTF: lane 2=Yeast-derived aglycosylated apo-rhTF; lane 3=rice-derived apo-rhTF; lane 4=native holo-hTF; lane 5=Yeast-derived aglycosylated holo-rhTF; 6=rice-derived holo-rhTF). It was shown that the rice-derived apo- or holo-rhTF migrated with the same mobility exhibited by their corresponding form of yeast-derived aglycosylated rhTF. These results showed that rice-derived rhTF was able to bind and release iron reversibly. However, both apo- and holo-native hTF exhibited faster mobility compared to their respective counterpart of recombinant hTF. The faster electrophoretic mobility of native hTF is associated with its possession of negatively charged sialic acid residues that are absent in both rice- and yeast-derived rhTFs.

Example 10

Cell Growth and Antibody Productivity Assay of rhTF

The rice-derived rhTF was compared to the native holo-hTF (Sigma, St. Louis, Mo.) to test its effect on proliferation and productivity of hybridoma cells under serum-free conditions. The log phase Sp2/0-derived hybridoma cells AE1 (ATCC HB-72) were prepared by growing in DMEM/F12 medium+1% FBS+ITSE supplement (insulin 10 μg/ml, TF 5.5 μg/ml, Sodium selenite 0.0067 μg/ml, ethanolamine 2.0 μg/ml (Invitrogen, Carlsbad, Calif.). The cells were then washed three times with DMEM/F12 without supplements to remove FBS and TF, and seeded in serum-free assay medium (DMEM/F12 supplemented with ISE (no TF) and 1 g/L CELLASTIM™ (recombinant human albumin) (InVitria, Fort Collins, Colo.)) at 0.8×105 viable cells/ml. A dose response study was carried out by adding rhTF or its native counterpart hTF (Sigma, St. Louis, Mo.) into assay medium at concentrations of 0.03, 0.1, 0.3, 1.0, 5.0, and 30 μg/ml and examining their cell proliferation effect after three days of growth in a humidified incubator, 37° C., 6% CO2. The negative control was the same assay medium without any added TF, while 10% FBS and ITSE cocktail (Invitrogen, Carlsbad, Calif.) in assay medium were positive controls. The assay was carried out in duplicate 1 ml stationary cultures for each condition. The concentration of viable cells was determined by a Guava PCA cell counter. The cell proliferation effect of rhTF was further evaluated by using cell growth curve. The AE1 cells were grown in assay medium with the addition of rhTF or native hTF at 10 μg/ml, and the concentration of viable cells was determined every day for six days.

The cell productivity of rhTF was assayed by quantifying the amount of antibody produced in hybridoma cells at day 6 through ELISA. After cells and debris were removed from the media by centrifugation, the antibody quantity was measured using by ELISA as instructed by the manufacturer (Bethyl Labs, Montgomery, Tex.).

Effect of rhTF on Cell Growth and Antibody Production

Figure 11:
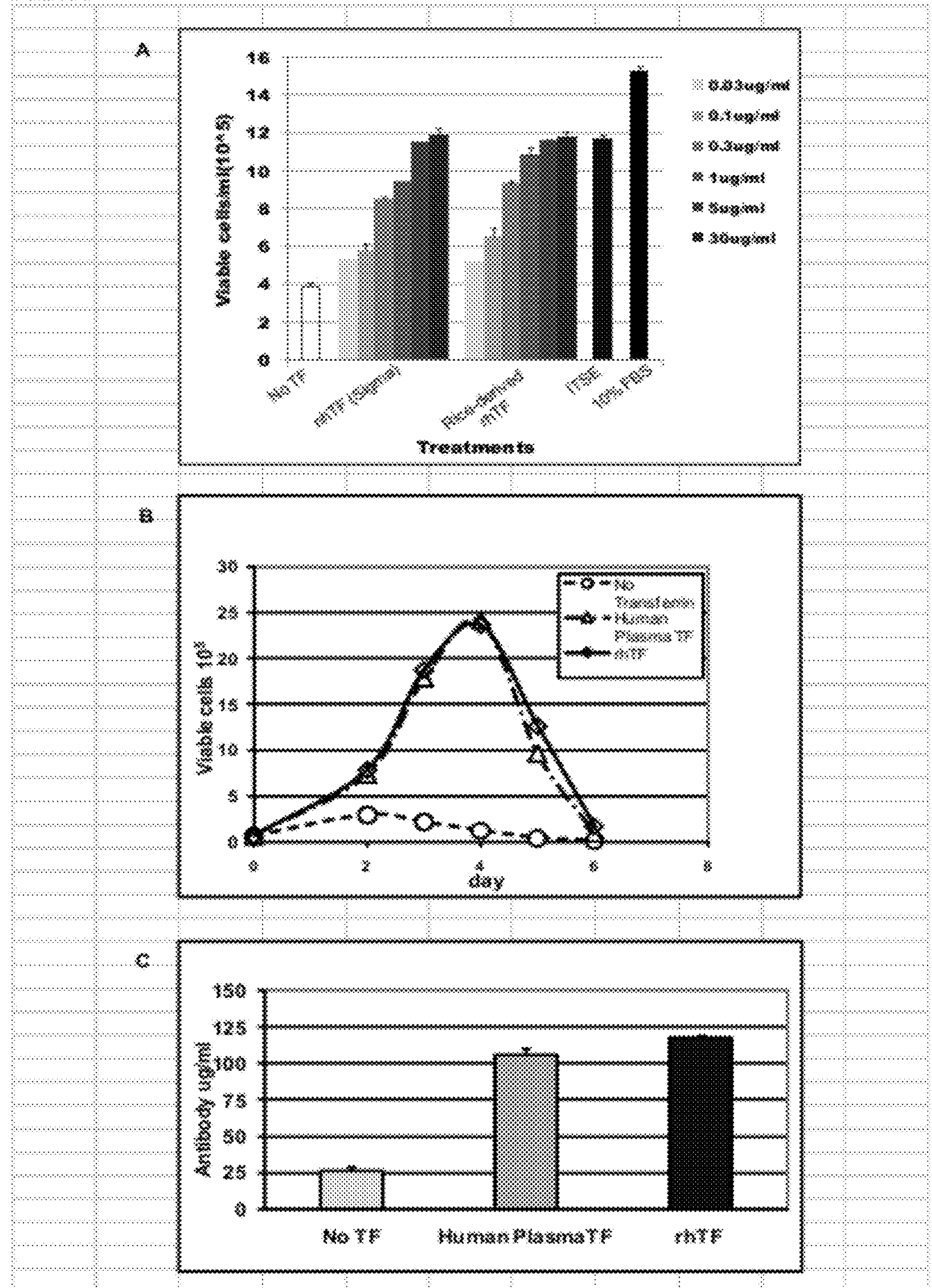
FIGS. 11A-C presents an analysis of the effect of rhTF on cell growth and antibody production.

Rice-derived pis-rhTF was shown to have an equivalent dose response as native holo-hTF for the proliferation of hybridoma cells (FIG. 11A shows viable cell concentration of hybridoma cells after three days in serum-free media supplemented with no hTF, 0.03, 0.1, 0.3, 1, 5 or 30 μg/ml native hTF (hobo form), rice-derived rhTF, ITSE or 10% FBS). Less than saturating levels of activity were observed at concentrations from 0.03 to 1 μg/ml with similar EC50 value of about 0.3 μg/ml. Likewise, a similar maximum effect was observed at 5 and 30 μg/ml that supported cell proliferation to 12.0×105 cells/ml. The maximum effect was similar to the ITSE cocktail control containing 5.5 μg/ml native hTF. In addition, hybridoma cells grown in medium with either rice-derived rhTF or native hTF showed similar growth curves (FIG. 11B shows 6 day growth curve of Sp2/0 hybridoma in serum-free medium with either 10 μg/ml native hTF or rice-derived rhTF, or unsupplemented), supporting that rhTF has the same proliferation effect as native hTF. Similar effects of rhTF and native hTF on production of antibody were also seen (FIG. 11C shows increase in antibody production by hybridoma cells in serum-free medium supplied with TF). These data show that pis-rhTF is equivalent to the native holo-form of hTF in stimulating cell growth and antibody production.

Likely, the pis-partially iron-saturated rhTF quickly becomes iron saturated due to the presence of iron in the medium.

While various specific embodiments have been illustrated and described in some detail for purposes of clarity of understanding, it will be appreciated by those of ordinary skill in the art in light of these teaching that various changes can be made without departing from the spirit and scope of the claims. Therefore, it is to be understood that the disclosure is not to be limited to the specific embodiments disclosed herein, as such are presented by way of example. It will also be apparent to those of ordinary skill in the art that each of the individual embodiments described and illustrated herein has discrete components and features which may be readily separated from or combined with the features of any of the other several embodiments without departing from the scope and spirit of the teachings. Although specific terms are employed herein, they are used in a generic and descriptive sense only and not for purposes of limitation.

All literature and similar materials cited in this application, including, but not limited to, patents, patent applications, articles, books, treatises, interne web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. A method of producing a recombinant, non-glycosylated transferrin protein in rice plant seeds, said method comprising the steps of:

(a) transforming a rice plant cell with a chimeric gene comprising (i) a promoter from a gene of a seed maturation-specific monocot plant storage protein;

(ii) a first DNA sequence, operably linked to said promoter, the first DNA sequence encoding a signal sequence targeting a polypeptide linked thereto to a protein storage body of a monocot plant seed cell; and (iii) a second DNA sequence, linked in translation frame with the first DNA sequence, encoding a mammalian transferrin protein, wherein the first DNA sequence and the second DNA sequence together encode a fusion protein comprising the signal sequence and the transferrin protein;

(b) growing a rice plant from the transformed rice plant cell for a time sufficient to produce seeds containing the transferrin protein; and (c) harvesting the seeds from the plant.

2. The method of claim 1, wherein the second DNA sequence encoding the mammalian transferrin protein encodes a human transferrin protein having the amino acid sequence identified by SEQ ID NO. 3.

3. The method of claim 1, wherein the second DNA sequence encoding the mammalian transferrin protein encodes a macaque transferrin protein having the amino acid sequence identified by SEQ ID NO. 27.

4. The method of claim 1, wherein the first DNA sequence encoding a signal sequence targeting a polypeptide linked thereto to a protein storage body of a monocot plant seed cell encodes a rice glutelin signal sequence.

5. The method of claim 1, wherein the promoter and signal sequence from the gene of a seed maturation-specific monocot plant storage protein encodes a glutelin (Gt1) promoter and signal sequence having the nucleic acid sequence identified by SEQ ID NO. 4.

6. A rice plant seed-derived composition, selected from the group consisting of a whole-seed composition, a flour composition, an extract composition and a malt composition, prepared from the harvested seeds obtained by the method of claim 1.

7. The seed-derived composition of claim 6, wherein the transferrin protein constitutes at least 0.1% of the dry weight of the seed-derived composition.

8. A seed-derived composition comprising a non-glycosylated transferrin protein, and at least one pharmaceutically acceptable excipient or nutrient, wherein the non-glycosylated transferrin protein is produced in a rice plant containing a nucleic acid sequence encoding the transferrin protein and is extracted from seed harvested from the rice plant.

9. A method for making a cell culture medium, said method comprising the steps of:

(a) obtaining a rice plant stably transformed with a chimeric gene having construct comprising (i) a seed maturation-specific promoter;

(ii) a leader DNA sequence encoding a transit sequence targeting a linked polypeptide to a protein storage body of a rice plant seed cell; wherein said leader DNA sequence is operably linked to said promoter;

(iii) a protein-coding sequence encoding a transferrin protein;

(b) cultivating the transformed plant under seed-maturation conditions;

(c) harvesting the seeds from the cultivated plant;

(d) extracting the harvested seeds with an aqueous solution, thereby obtaining an extract of water soluble plant components comprising at least 3% by total protein weight of non-glycosylated transferrin protein;

(e) purifying the transferrin protein from the aqueous solution; and (f) adding the purified transferrin protein to a cell culture medium.

10. The method of claim 1, wherein the protein-coding sequence encodes human transferrin.

11. The method of claim 10, wherein the human transferrin protein-coding sequence is the codon-optimized sequence identified by SEQ ID NO: 2.

12. The method of claim 10, wherein the transformed rice plant further comprises a nucleic acid that encodes at least one transcription factor selected from the group consisting of Rice endosperm bZIP (Reb) (encoded by the sequence set forth as SEQ ID NO: 22), Opaque 2 (O2) (encoded by the sequence set forth as SEQ ID NO: 20) and prolamin box binding factor (PBF) (encoded by the sequence set forth as SEQ ID NO: 21).

13. The method of claim 12, wherein the transcription factor is O2 and/or PBF.

14. A serum-free cell culture medium comprising an extract of rice seed comprising seed-expressed non-glycosylated transferrin protein.

15. The method of claim 1, wherein the transferrin protein constitutes at least 0.01% seed weight of the harvested seeds.

16. The method of claim 1, wherein the signal sequence in the fusion protein is located at the N-terminus.

17. A transformed rice plant produced according to the method of claim 1.

18. A transformed rice seed produced according to the method of claim 1.

* * * * *

SEQUENCE LISTING

```
<160> NUMBER OF SEQ ID NOS: 28

<210> SEQ ID NO 1
<211> LENGTH: 2037
<212> TYPE: DNA
<213> ORGANISM: Homo sapiens
<220> FEATURE:
<223> OTHER INFORMATION: native human transferrin gene

<400> SEQUENCE: 1

gtccctgata aaactgtgag atggtgtgca gtgtcggagc atgaggccac taagtgccag     60

agtttccgcg accatatgaa aagcgtcatt ccatccgatg gtcccagtgt tgcttgtgtg    120

aagaaagcct cctaccttga ttgcatcagg gccattgcgg caaacgaagc ggatgctgtg    180

acactggatg caggtttggt gtatgatgct tacttggctc ccaataacct gaagcctgtg    240

gtggcagagt tctatgggtc aaaagaggat ccacagactt tctattatgc tgttgctgtg    300

gtgaagaagg atagtggctt ccagatgaac cagcttcgag gcaagaagtc ctgccacacg    360

ggtctaggca ggtccgctgg gtggaacatc cccataggct tactttactg tgacttacct    420

gagccacgta aacctcttga gaaagcagtg gccaatttct tctcgggcag ctgtgcccct    480

tgtgcggatg ggacggactt cccccagctg tgtcaactgt gtccagggtg tggctgctcc    540

acccttaacc aatacttcgg ctactcggga gccttcaagt gtctgaagga tggtgctggg    600

gatgtggcct ttgtcaagca ctcgactata tttgagaact tggcaaacaa ggctgacagg    660

gaccagtatg agctgctttg cctagacaac acccggaagc cggtagatga atacaaggac    720

tgccacttgg cccaggtccc ttctcatacc gtcgtggccc gaagtatggg cggcaaggag    780

gacttgatct gggagcttct caaccaggcc caggaacatt ttggcaaaga caaatcaaaa    840

gaattccaac tattcagctc tcctcatggg aaggacctgc tgtttaagga ctctgcccac    900

gggtttttaa aagtcccccc aaggatggat gccaagatgt acctgggcta tgagtatgtc    960

actgccatcc ggaatctacg ggaaggcaca tgcccagaag ccccaacaga tgaatgcaag   1020

cctgtgaagt ggtgtgcgct gagccaccac gagaggctca agtgtgatga gtggagtgtt   1080

aacagtgtag ggaaaataga gtgtgtatca gcagagacca ccgaagactg catcgccaag   1140

atcatgaatg gagaagctga tgccatgagc ttggatggag ggtttgtcta catagcgggc   1200

aagtgtggtc tggtgcctgt cttggcagaa aactacaata agagcgataa ttgtgaggat   1260

acaccagagg cagggtattt tgctgtagca gtggtgaaga aatcagcttc tgacctcacc   1320

tgggacaatc tgaaaggcaa gaagtcctgc catacggcag ttggcagaac cgctggctgg   1380

aacatcccca tgggcctgct ctacaataag atcaaccact gcagatttga tgaatttttc   1440
```

```
agtgaaggtt gtgcccctgg gtctaagaaa gactccagtc tctgtaagct gtgtatgggc   1500

tcaggcctaa acctgtgtga acccaacaac aaagagggat actacggcta cacaggcgct   1560

ttcaggtgtc tggttgagaa gggagatgtg gcctttgtga aacaccagac tgtcccacag   1620

aacactgggg gaaaaaaccc tgatccatgg gctaagaatc tgaatgaaaa agactatgag   1680

ttgctgtgcc ttgatggtac caggaaacct gtggaggagt atgcgaactg ccacctggcc   1740

agagccccga atcacgctgt ggtcacacgg aaagataagg aagcttgcgt ccacaagata   1800

ttacgtcaac agcagcacct atttggaagc aacgtaactg actgctcggg caacttttgt   1860

ttgttccggt cggaaaccaa ggaccttctg ttcagagatg acacagtatg tttggccaaa   1920

cttcatgaca gaaacacata tgaaaaatac ttaggagaag aatatgtcaa ggctgttggt   1980

aacctgagaa aatgctccac ctcatcactc ctggaagcct gcactttccg tagacct      2037
```

```
<210> SEQ ID NO 2
<211> LENGTH: 2037
<212> TYPE: DNA
<213> ORGANISM: Artificial Sequence
<220> FEATURE:
<223> OTHER INFORMATION: codon optimized human transferrin gene

<400> SEQUENCE: 2
```

```
gtccctgaca agaccgtgag gtggtgcgcc gtgtccgagc acgaggccac caagtgccag     60

agcttccgcg accacatgaa gagcgtcatc ccgtccgacg ggccgtcggt cgcgtgcgtg    120

aagaaggcct cctacctcga ctgcatcagg gccatcgcgg ccaacgaggc ggacgccgtg    180

accctggacg cgggcctcgt gtacgacgcc tacctcgcgc ccaacaacct gaagccggtg    240

gtggccgagt tctacgggtc caaggaggac ccgcagacgt tctactacgc cgtcgccgtg    300

gtgaagaagg acagcggctt ccagatgaac cagctcaggg gcaagaagtc ctgccacacc    360

ggcctcggca ggtccgcggg ctggaacatc ccgatcggcc tgctctactg cgacctcccg    420

gagccgcgca agccgctgga gaaggccgtg gccaacttct tctcgggctc ctgcgccccg    480

tgcgccgacg gcacggactt cccgcagctg tgccagctgt gcccggggtg cggctgctcc    540

accctgaacc agtacttcgg ctactccggc gccttcaagt gcctgaagga cggcgcgggc    600

gacgtggcct tcgtcaagca ctccaccatc ttcgagaacc tcgcgaacaa ggccgacagg    660

gaccagtacg agctcctgtg cctcgacaac accaggaagc cggtcgacga gtacaaggac    720

tgccacctcg cccaggtccc gagccacacc gtcgtggccc gctccatggg cggcaaggag    780

gacctcatct gggagctgct caaccaggcc caggagcatt tcggcaagga caagtccaag    840

gagttccagc tgttcagctc ccgcacgggg aaggacctgc tgttcaagga ttccgcccac    900

gggttcctca aggtcccccc gaggatggac gccaagatgt acctgggcta cgagtacgtg    960

accgccatcc gcaacctccg cgagggcacc tgcccggagg ccccgacgga cgagtgcaag   1020

cccgtgaagt ggtgcgcgct gagccaccac gagaggctca agtgcgacga gtggtccgtg   1080

aactccgtcg gcaagatcga gtgcgtcagc gccgagacca ccgaggactg catcgccaag   1140

atcatgaacg gggaggccga cgccatgagc ctggacgggg gcttcgtcta catcgcgggc   1200

aagtgcggac tggtgccggt cctcgccgag aactacaaca agagcgacaa ctgcgaggac   1260

accccggagg ccggctactt cgccgtggcg gtggtgaaga agtccgccag cgacctcacc   1320

tgggacaacc tcaagggcaa gaagtcctgc cacaccgccg tcggcaggac cgccggctgg   1380

aacatcccga tgggcctgct ctacaacaag atcaaccact gcaggttcga cgagttcttc   1440
```

```
agcgagggct gcgccccggg gagcaagaag gacagctcgc tctgcaagct gtgcatgggc   1500

agcggcctca acctgtgcga gcccaacaac aaggaggggt actacggcta caccggcgcg   1560

ttcaggtgcc tcgtcgagaa gggcgacgtg gccttcgtga agcaccagac cgtcccgcag   1620

aacaccggcg ggaagaaccc ggacccgtgg gccaagaacc tcaacgagaa ggactacgag   1680

ctgctgtgcc tcgacggcac caggaagccc gtggaggagt acgcgaactg ccacctggcc   1740

cgcgccccga accacgcggt ggtcacaagg aaggataagg aggcctgcgt ccacaagatc   1800

ctgaggcaac agcagcacct cttcggcagc aacgtcaccg actgcagcgg caacttctgc   1860

ctcttcaggt cggagaccaa ggacctcctg ttcagggatg acacggtctg cctcgccaag   1920

ctgcacgacc gcaacaccta cgagaagtac ctcggcgagg agtacgtcaa ggcggtgggc   1980

aacctgagga agtgctccac ctccagcctc ctggaggcct gcacgttcag gcgcccg      2037


<210> SEQ ID NO 3
<211> LENGTH: 698
<212> TYPE: PRT
<213> ORGANISM: Homo sapiens
<220> FEATURE:
<223> OTHER INFORMATION: mature human TF Swiss-Prot P02787

<400> SEQUENCE: 3

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
```

```
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685
```

```
Leu Leu Glu Ala Cys Thr Phe Arg Arg Pro
    690                 695


<210> SEQ ID NO 4
<211> LENGTH: 786
<212> TYPE: DNA
<213> ORGANISM: Oryza sativa
<220> FEATURE:
<223> OTHER INFORMATION: Rice Gt1 promoter and Gt1 leader coding
      sequence

<400> SEQUENCE: 4

catgagtaat gtgtgagcat tatgggacca cgaaataaaa agaacatttt gatgagtcgt     60

gtatcctcga tgagcctcaa aagttctctc accccggata agaaaccctt aagcaatgtg    120

caaagtttgc attctccact gacataatgc aaaataagat atcatcgatg acatagcaac    180

tcatgcatca tatcatgcct ctctcaacct attcattcct actcatctac ataagtatct    240

tcagctaaat gttagaacat aaacccataa gtcacgtttg atgagtatta ggcgtgacac    300

atgacaaatc acagactcaa gcaagataaa gcaaaatgat gtgtacataa aactccagag    360

ctatatgtca tattgcaaaa agaggagagc ttataagaca aggcatgact cacaaaaatt    420

cacttgcctt tcgtgtcaaa aagaggaggg ctttacatta tccatgtcat attgcaaaag    480

aaagagagaa agaacaacac aatgctgcgt caattataca tatctgtatg tccatcatta    540

ttcatccacc tttcgtgtac cacacttcat atatcataag agtcacttca cgtctggaca    600

ttaacaaact ctatcttaac atttagatgc aagagccttt atctcactat aaatgcacga    660

tgatttctca ttgtttctca caaaaagcgg ccgcttcatt agtcctacaa caacatggca    720

tccataaatc gccccatagt tttcttcaca gtttgcttgt tcctcttgtg cgatggctcc    780

ctagcc                                                                786


<210> SEQ ID NO 5
<211> LENGTH: 1055
<212> TYPE: DNA
<213> ORGANISM: Oryza sativa
<220> FEATURE:
<223> OTHER INFORMATION: Rice Glb promoter and Gt1 leader coding
      sequence

<400> SEQUENCE: 5

ctgcagggag gagaggggag agatggtgag agaggaggaa gaagaggagg ggtgacaatg     60

atatgtgggg catgtgggca cccaattttt taattcattc ttttgttgaa actgacatgt    120

gggtcccatg agatttatta tttttcggat cgaatcgcca cgtaagcgct acgtcaatgc    180

tacgtcagat gaagaccgag tcaaattagc cacgtaagcg ccacgtcagc caaaaccacc    240

atccaaaccg ccgagggacc tcatctgcac tggttttgat agttgaggga cccgttgtat    300

ctggtttttc gattgaagga cgaaaatcaa atttgttgac aagttaaggg accttaaatg    360

aacttattcc atttcaaaat attctgtgag ccatatatac cgtgggcttc caatcctcct    420

caaattaaag ggccttttta aaatagataa ttgccttctt tcagtcaccc ataaaagtac    480

aaaactacta ccaacaagca acatgcgcag ttacacacat tttctgcaca tttccgccac    540

gtcacaaaga gctaagagtt atccctagga caatctcatt agtgtagata catccattaa    600

tcttttatca gaggcaaacg taaagccgct ctttatgaca aaaataggtg acacaaaagt    660

gttatctgcc acatacataa cttcagaaat tacccaacac caagagaaaa ataaaaaaaa    720

atctttttgc aagctccaaa tcttggaaac ctttttcact ctttgcagca ttgtactctt    780
```

```
gctctttttc caaccgatcc atgtcaccct caagcttcta cttgatctac acgaagctca    840

ccgtgcacac aaccatggcc acaaaaaccc tataaaaccc catccgatcg ccatcatctc    900

atcatcagtt cattaccaac aaacaaaaga ggaaaaaaaa catatacact tctagtgatt    960

gtctgattga tcatcaatct agaggcggcc gcatggctag caaggtcgtc ttcttcgcgg   1020

cggcgctcat ggcggccatg gtggccatct ccggc                              1055
```

```
<210> SEQ ID NO 6
<211> LENGTH: 976
<212> TYPE: DNA
<213> ORGANISM: Artificial Sequence
<220> FEATURE:
<223> OTHER INFORMATION: Bx7 promoter seq

<400> SEQUENCE: 6

ctgcaggcca gggaaagaca atggacatgc aaagaggtag gggcagggaa gaaacacttg     60

gagatcatag aagaacataa gaggttaaac ataggagggc ataatggaca attaaatcta    120

cattaattga actcatttgg gaagtaaaca aaatccatat tctggtgtaa atcaaactat    180

ttgacgcgga tttactaaga tcctatgtta attttagaca tgactggcca aaggtttcag    240

ttagttcatt tgtcacggaa aggtgttttc ataagtccaa aactctacca actttttttgc   300

acgtcatagc atagatagat gttgtgagtc attggataga tattgtgagt cagcatggat    360

ttgtgttgcc tggaaatcca actaaatgac aagcaacaaa acctgaaatg ggctttagga    420

gagatggttt atcaatttac atgttccatg caggctacct tccactactc gacatggtta    480

gaagttttga gtgccgcata tttgcggaag caatggcact actcgacatg gttagaagtt    540

ttgagtgccg catatttgcg gaagcaatgg ctaacagata catattctgc caaaccccaa    600

gaaggataat cactcctctt agataaaaag aacagaccaa tgtacaaaca tccacacttc    660

tgcaaacaat acaccagaac taggattaag cccattacgt ggctttagca gaccgtccaa    720

aaatctgttt tgcaagcacc aattgctcct tacttatcca gcttcttttg tgttggcaaa    780

ctgccctttt ccaaccgatt ttgtttcttc tcacgctttc ttcataggct aaactaacct    840

cggcgtgcac acaaccatgt cctgaacctt cacctcgtcc ctataaaagc ccatccaacc    900

ttacaatctc atcatcaccc acaacaccga gcaccccaat ctacagatca attcactgac    960

agttcactga tctaga                                                    976
```

```
<210> SEQ ID NO 7
<211> LENGTH: 1009
<212> TYPE: DNA
<213> ORGANISM: Artificial Sequence
<220> FEATURE:
<223> OTHER INFORMATION: Glub-2  promoter seq

<400> SEQUENCE: 7

ctgcagtaat ggatacctag tagcaagcta gcttaaacaa atctaaattc caatctgttc     60

gtaaacgttt tctcgatcgc aattttgatc aaaactattg aaaacctcaa ttaaaccatt    120

caaaattttt aatataccca acaagagcgt ccaaaccaaa tatgtaaata tggatgtcat    180

gataattgac ttatgacaat gtgattattt catcaagtct ttaaatcatt aattctagtt    240

gaaggtttat gttttcttat gctaaagggt tatgtttata taagaatatt aaagagcaaa    300

ttgcaataga tcaacacaac aaatttgaat gtttccagat gtgtaaaaat atccaaatta    360

attgttttaa aatagtttta agaaggatct gatatgcaag tttgatagtt agtaaactgc    420
```

```
aaaagggctt attacatgga aaattcctta ttgaatatgt ttcattgact ggtttatttt    480

acatgacaac aaagttacta gtatgtcaat aaaaaaatac aaggttactt gtcaattgta    540

ttgtgccaag taaagatgac aacaaacata caaatttatt tgttctttta tagaaacacc    600

taacttatca aggatagttg gccacgcaaa aatgacaaca tactttacaa ttgtatcatc    660

ataaagatct tatcaagtat aagaacttta tggtgacata aaaaataatc acaagggcaa    720

gacacatact aaaagtatgg acagaaattt cttaacaaac tccatttgtt ttgtatccaa    780

aagcataaga aatgagtcat ggctgagtca tgatatgtag ttcaatcttg caaaattgcc    840

tttttgttaa gtattgtttt aacactacaa gtcacatatt gtctatactt gcaacaaaca    900

ctattaccgt gtatcccaag tggccttttc attgctatat aaactagctt gatcggtctt    960

tcaactcaca tcaattagct taagtttcca ttagcaactg ctaatagct               1009
```

<210> SEQ ID NO 8
<211> LENGTH: 839
<212> TYPE: DNA
<213> ORGANISM: Artificial Sequence
<220> FEATURE:
<223> OTHER INFORMATION: Gt3 promoter seq

<400> SEQUENCE: 8

```
ctgcagtgta agtgtagctt cttatagctt agtgctttac tatcttcaca agcacatgct     60

atagtattgt tccaagatga aagaataatt catccttgct accaacttgc atgatattat    120

atttgtgaat atcctatctc ttggcttata atgaaatgtg ctgctgggtt attctgacca    180

tggtatttga gagcctttgt atagctgaaa ccaacgtata tcgagcatgg aacagagaac    240

aaaatgcaag gatttttta ttctggttca tgccctggat gggttaatat cgtgatcatc     300

aaaaaagata tgcataaaat taaagtaata aatttgctca taagaaacca aaaccaaaag    360

cacatatgtc ctaaacaaac tgcattttgt ttgtcatgta gcaatacaag agataatata    420

tgacgtggtt atgacttatt cactttttgt gactccaaaa tgtagtaggt ctaactgatt    480

gtttaaagtg atgtcttact gtagaagttt catcccaaaa gcaatcacta aagcaacaca    540

cacgtatagt ccaccttcac gtaattcttt gtggaagata acaagaaggc tcactgaaaa    600

ataaaagcaa agaaaaggat atcaaacaga ccattgtgca tcccattgat ccttgtatgt    660

ctatttatct atcctccttt tgtgtacctt acttctatct agtgagtcac ttcatatgtg    720

gacattaaca aactctatct taacatctag tcgatcacta ctttacttca ctataaaagg    780

accaacatat atcatccatt tctcacaaaa gcattgagtt cagtcccaca aaatctaga     839
```

<210> SEQ ID NO 9
<211> LENGTH: 1302
<212> TYPE: DNA
<213> ORGANISM: Artificial Sequence
<220> FEATURE:
<223> OTHER INFORMATION: Glub-1 promoter seq

<400> SEQUENCE: 9

```
ctgcagagat atggattttc taagattaat tgattctctg tctaaagaaa aaaagtatta     60

ttgaattaaa tggaaaaaga aaaaggaaaa aggggatggc ttctgctttt tgggctgaag    120

gcggcgtgtg gccagcgtgc tgcgtgcgga cagcgagcga acacacgacg gagcagctac    180

gacgaacggg ggaccgagtg gaccggacga ggatgtggcc taggacgagt gcacaaggct    240

agtggactcg gtccccgcgc ggtatcccga gtggtccact gtctgcaaac acgattcaca    300

tagagcgggc agacgcggga gccgtcctag gtgcaccgga agcaaatccg tcgcctgggt    360
```

```
ggatttgagt gacacggccc acgtgtagcc tcacagctct ccgtggtcag atgtgtaaaa    420

ttatcataat atgtgttttt caaatagtta aataatatat ataggcaagt tatatgggtc    480

aataagcagt aaaaaggctt atgacatggt aaaattactt acaccaatat gccttactgt    540

ctgatatatt ttacatgaca acaaagttac aagtacgtca tttaaaaata caagttactt    600

atcaattgta gtgtatcaag taaatgacaa caaacctaca aatttgctat tttgaaggaa    660

cacttaaaaa aatcaatagg caagttatat agtcaataaa ctgcaagaag gcttatgaca    720

tggaaaaatt acatacacca atatgcttta ttgtccggta tattttacaa gacaacaaag    780

ttataagtat gtcatttaaa aatacaagtt acttatcaat tgtcaagtaa atgaaaacaa    840

acctacaaat ttgttatttt gaaggaacac ctaaattatc aaatatagct tgctacgcaa    900

aatgacaaca tgcttacaag ttattatcat cttaaagtta gactcatctt ctcaagcata    960

agagctttat ggtgcaaaaa caaatataat gacaaggcaa agatacatac atattaagag   1020

tatggacaga catttcttta acaaactcca tttgtattac tccaaaagca ccagaagttt   1080

gtcatggctg agtcatgaaa tgtatagttc aatcttgcaa agttgccttt ccttttgtac   1140

tgtgttttaa cactacaagc catatattgt ctgtacgtgc aacaaactat atcaccatgt   1200

atcccaagat gctttttat tgctatataa actagcttgg tctgtctttg aactcacatc   1260

aattagctta agtttccata agcaagtaca aatagctcta ga                        1302
```

<210> SEQ ID NO 10
<211> LENGTH: 675
<212> TYPE: DNA
<213> ORGANISM: Oryza sativa
<220> FEATURE:
<223> OTHER INFORMATION: Rice prolamin promoter seq

<400> SEQUENCE: 10

```
ctgcagcatc ggcttaggtg tagcaacacg actttattat tattattatt attattatta     60

ttattttaca aaaatataaa atagatcagt ccctcaccac aagtagagca agttggtgag    120

ttattgtaaa gttctacaaa gctaatttaa aagttattgc attaacttat ttcatattac    180

aaacaagagt gtcaatggaa caatgaaaac catatgacat actataattt tgtttttatt    240

attgaaatta tataattcaa agagaataaa tccacatagc cgtaaagttc tacatgtggt    300

gcattaccaa aatatatata gcttacaaaa catgacaagc ttagtttgaa aaattgcaat    360

ccttatcaca ttgacacata aagtgagtga tgagtcataa tattattttt cttgctaccc    420

atcatgtata tatgatagcc acaaagttac tttgatgatg atatcaaaga acatttttag    480

gtgcacctaa cagaatatcc aaataatatg actcacttag atcataatag agcatcaagt    540

aaaactaaca ctctaaagca accgatggga aagcatctat aaatagacaa gcacaatgaa    600

aatcctcatc atccttcacc acaattcaaa tattatagtt gaagcatagt agtagaatcc    660

aacaacaatc tagag                                                      675
```

<210> SEQ ID NO 11
<211> LENGTH: 1098
<212> TYPE: DNA
<213> ORGANISM: Oryza sativa
<220> FEATURE:
<223> OTHER INFORMATION: Rice cysteine peptidase promoter seq

<400> SEQUENCE: 11

```
ccaggcttca tcctaaccat tacaggcaag atgttgtatg aagaagggcg aacatgcaga     60
```

```
ttgttaaact gacacgtgat ggacaagaat gaccgattgg tgaccggtct gacaatggtc    120

atgtcgtcag cagacagcca tctcccacgt cgcgcctgct tccggtgaaa gtggaggtag    180

gtatgggccg tcccgtcaga aggtgattcg gatggcagcg atacaaatct ccgtccatta    240

atgaagagaa gtcaagttga aagaaaggga gggagagatg gtgcatgtgg gatccccttg    300

ggatataaaa ggaggacctt gcccacttag aaaggagagg agaaagcaat cccagaagaa    360

tcgggggctg actggcactt tgtagcttct tcatacgcga atccaccaaa acacaggagt    420

agggtattac gcttctcagc ggcccgaacc tgtatacatc gcccgtgtct tgtgtgtttc    480

cgctcttgcg aaccttccac agattgggag cttagaacct cacccagggc ccccggccga    540

actggcaaag gggggcctgc gcggtctccc ggtgaggagc cccacgctcc gtcagttcta    600

aattacccga tgagaaaggg aggggggggg gggaaatctg ccttgtttat ttacgatcca    660

acggatttgg tcgacaccga tgaggtgtct taccagttac cacgagctag attatagtac    720

taattacttg aggattcggt tcctaatttt ttacccgatc gacttcgcca tggaaaattt    780

tttattcggg ggagaatatc caccctgttt cgctcctaat taagatagga attgttacga    840

ttagcaacct aattcagatc agaattgtta gttagcggcg ttggatccct cacctcatcc    900

catcccaatt cccaaaccca aactcctctt ccagtcgccg acccaaacac gcatccgccg    960

cctataaatc ccacccgcat cgagcctatc aagcccaaaa aaccacaaac caaacgaaga   1020

aggaaaaaaa aaggaggaaa agaaaagagg aggaaagcga agaggttgga gagagacgct   1080

cgtctccacg tcgccgcc                                                 1098
```

<210> SEQ ID NO 12
<211> LENGTH: 432
<212> TYPE: DNA
<213> ORGANISM: Hordeum vulgare
<220> FEATURE:
<223> OTHER INFORMATION: Barley D-Hordein promoter

<400> SEQUENCE: 12

```
cttcgagtgc ccgccgattt gccagcaatg gctaacagac acatattctg ccaaaacccc     60

agaacaataa tcacttctcg tagatgaaga gaacagacca agatacaaac gtccacgctt    120

cagcaaacag taccccagaa ctaggattaa gccgattacg cggctttagc agaccgtcca    180

aaaaaactgt tttgcaaagc tccaattcct ccttgcttat ccaatttctt ttgtgttggc    240

aaactgcact tgtccaaccg attttgttct tcccgtgttt cttcttaggc taactaacac    300

agccgtgcac atagccatgg tccggaatct tcacctcgtc cctataaaag cccagccaat    360

ctccacaatc tcatcatcac cgagaacacc gagaaccaca aaactagaga tcaattcatt    420

gacagtccac cg                                                        432
```

<210> SEQ ID NO 13
<211> LENGTH: 60
<212> TYPE: DNA
<213> ORGANISM: Artificial Sequence
<220> FEATURE:
<223> OTHER INFORMATION: bx7 signal peptide sequence

<400> SEQUENCE: 13

```
atggctaagc gcctggtcct ctttgcggca gtagtcgtcg ccctcgtggc tctcaccgcc     60
```

<210> SEQ ID NO 14
<211> LENGTH: 72
<212> TYPE: DNA
<213> ORGANISM: Artificial Sequence

```
<220> FEATURE:
<223> OTHER INFORMATION: Glub-2  signal peptide sequence

<400> SEQUENCE: 14

atggcaacta ccattttctc tcgtttttct atatactttt gtgctatgct attatgccag     60

ggttctatgg cc                                                         72


<210> SEQ ID NO 15
<211> LENGTH: 85
<212> TYPE: DNA
<213> ORGANISM: Artificial Sequence
<220> FEATURE:
<223> OTHER INFORMATION: Gt3  signal peptide sequence

<400> SEQUENCE: 15

atgtggacat taacaaactc tatcttaaca tctagtcgat cactacttta cttcactata     60

aaaggaccaa catatatcat ccatt                                           85


<210> SEQ ID NO 16
<211> LENGTH: 72
<212> TYPE: DNA
<213> ORGANISM: Artificial Sequence
<220> FEATURE:
<223> OTHER INFORMATION: Glub-1 signal peptide sequence

<400> SEQUENCE: 16

atggcgagtt ccgttttctc tcggttttct atatactttt gtgttcttct attatgccat     60

ggttctatgg cc                                                         72


<210> SEQ ID NO 17
<211> LENGTH: 69
<212> TYPE: DNA
<213> ORGANISM: Artificial Sequence
<220> FEATURE:
<223> OTHER INFORMATION: prolamin signal peptide sequence

<400> SEQUENCE: 17

atgaagatca ttttcgtatt tgctctcctt gctattgttg catgcaacgc ttctgcacgg     60

tttgatgct                                                             69


<210> SEQ ID NO 18
<211> LENGTH: 63
<212> TYPE: DNA
<213> ORGANISM: Oryza sativa
<220> FEATURE:
<223> OTHER INFORMATION: Rice cysteine peptidase signal peptide sequence

<400> SEQUENCE: 18

atggccgccc gcgccgccgc cgccgcgttc ctgctgctgc tcatcgtcgt tggtcaccgc     60

gcc                                                                   63


<210> SEQ ID NO 19
<211> LENGTH: 63
<212> TYPE: DNA
<213> ORGANISM: Artificial Sequence
<220> FEATURE:
<223> OTHER INFORMATION: D- Hordein signal peptide sequence

<400> SEQUENCE: 19

atggctaagc ggctggtcct ctttgtggcg gtaatcgtcg ccctcgtggc tctcaccacc     60

gcc                                                                   63
```

<210> SEQ ID NO 20
<211> LENGTH: 1314
<212> TYPE: DNA
<213> ORGANISM: Zea mays
<220> FEATURE:
<223> OTHER INFORMATION: O2 transcription factor

<400> SEQUENCE: 20

```
atggagcacg tcatctcaat ggaggagatc ctcgggccct tctgggagct gctaccaccg      60

ccagcgccag agccagagcg agagcagcct ccggtaaccg gcatcgtcgt cggcagtgtc     120

atagacgttg ctgctgctgg tcatggtgac ggggacatga tggatcagca gcacgccaca     180

gagtggacct ttgagaggtt actagaagag gaggctctga cgacaagcac accgccgccg     240

gtggtggtgg tgccgaactc ttgttgctca ggcgccctaa atgctgaccg gccgccggtg     300

atggaagagg cggtaactat ggcgcctgcg gcggtgagta gtgccgtagt aggtgacccc     360

atggagtaca atgccatact gaggaggaag ctggaggagg acctcgaggc cttcaaaatg     420

tggagggcgg cctccagtgt tgtgacctca gatcaacgtt ctcaaggctc aaacaatcac     480

actggaggta gcagcatcag gaataatcca gtgcagaaca agctgatgaa cggcgaagat     540

ccaatcaaca ataaccacgc tcaaactgca ggccttggcg tgaggcttgc tactagctct     600

tcctcgagag atccttcacc atcagacgaa gacatggacg gagaagtaga gattctgggg     660

ttcaagatgc ctaccgagga aagagtgagg aaaagaaagg aatccaatag agaatcagcc     720

agacgctcga gatacaggaa agccgctcac ctgaaagaac tggaagacca ggtagcacag     780

ctaaaagccg agaattcttg cctgctgagg cgcattgccg ctctgaacca gaagtacaac     840

gacgctaacg tcgacaacag ggtgctgaga gcggacatgg agaccctaag agctaaggtg     900

aagatgggag aggactctct gaagcgggtg atagagatga gctcatcagt gccgtcgtcc     960

atgcccatct cggcgccgac ccccagctcc gacgctccag tgccgccgcc gcctatccga    1020

gacagcatcg tcggctactt ctccgccaca gccgcagacg acgatgcttc ggtcggcaac    1080

ggtttcttgc gactgcaagc tcatcaagag cctgcatcca tggtcgtcgg tggaactctg    1140

agcgccacag agatgaaccg agtagcagca gccacgcatt gcgcgggggc catggagcac    1200

atccagacgg cgatgggatc catgccgccg acctccgcct ccggatctac accgccgccg    1260

caggattatg agctgctggg tccaaatggg gccatacaca tggacatgta ttag          1314
```

<210> SEQ ID NO 21
<211> LENGTH: 987
<212> TYPE: DNA
<213> ORGANISM: Zea mays
<220> FEATURE:
<223> OTHER INFORMATION: PBF transcription factor

<400> SEQUENCE: 21

```
atggacatga tctccggcag cactgcagca acatcaacac cccacaacaa ccaacaggcg      60

gtgatgttgt catcccccat tataaaggag gaagctaggg acccaaagca gacacgagcc     120

atgccccaaa taggtggcag tggggagcgt aagccgaggc cgcaactacc tgaggcgctc     180

aagtgcccac gctgcgactc caacaacacc aagttttgct actacaacaa ttatagcatg     240

tcacaaccac gctacttttg caaggcttgc cgccgctatt ggacacatgg tggtaccctc     300

cgcaatgtcc ccattggtgg tgggtgtcgc aagaacaaac atgcctctag atttgtcttg     360

ggctctcaca cctcatcgtc ctcatctgct acctatgcac cattatcccc tagcaccaac     420

gctagctcta gcaatatgag catcaacaaa catatgatga tggtgcctaa catgacgatg     480
```

```
cctaccccaa cgacaatggg cttattccct aatgtgctcc caacacttat gccgacaggt    540

ggaggcgggg gctttgactt cactatggac aaccaacata gatcattgtc cttcacacca    600

atgtctctac ctagccaggg gccagtgcct atgctggctg caggagggag tgaggcaaca    660

ccgtctttcc tagagatgct gagaggaggg atttttcatg gtagtagtag ctataacaca    720

agtctcacga tgagtggtgg caacaatgga atggacaagc cattttcgct gccatcatat    780

ggtgcaatgt gcacaaatgg gttgagtggc tcaaccacta atgatgccag acaactggtg    840

gggcctcagc aggataacaa ggccatcatg aagagcagta ataacaacaa tggtgtatca    900

ttgttgaacc tctactggaa caagcacaac aacaacaaca acaacaacaa caacaacaac    960

aacaacaaca acaacaaggg acaataa                                         987
```

```
<210> SEQ ID NO 22
<211> LENGTH: 3902
<212> TYPE: DNA
<213> ORGANISM: Oryza sativa
<220> FEATURE:
<223> OTHER INFORMATION: Reb transcription factor

<400> SEQUENCE: 22

atggagcggg tgttctccgt ggaggagatc tccgacccat tctgggtccc gcctccgccg      60

ccgcagtcgg cggcggcggc ccagcagcag ggcggcggcg gcgtggcttc gggaggtggt    120

ggtggtgtag cggggggcgg cggcggcggg aacgcgatga accggtgccc gtcggagtgg    180

tacttccaga agtttctgga ggaggcggtg ctcgatagcc ccgtcccgaa ccctagcccg    240

agggccgaag cgggagggat caggggcgca ggaggggtgg tgccggtcga tgttaagcag    300

ccgcagctct cggcggcggc gacgacgagc gcggtggtgg accccgtgga gtacaacgcg    360

atgctgaagc agaagctgga gaaggacctc gccgcggtcg ccatgtggag ggtacagcca    420

ttctcccccc ctctagtact cgagagctta ctgagatcgg caatgctagc tactgtttgc    480

atcgaatgtt tataggtatt tagatcgggc atttctatag accaatggcg tccatggtct    540

tgcaatgcgc tctgttgagt gtcggtggtt ggttcgactc atagtatgta gggttgtgcg    600

tatgtacaaa cggaagcttc atagacctcg gtattgagat tgcgatatcg atgcaacctg    660

cgaattggcg atgtaatcag tcatattctt actaaactgc gagacagtgg tttgtttgca    720

attgcaatat ttttgtatgg ggctgcttaa actgtcattg cctttttaga ttggcaatat    780

gtgactttat gcaagtattt gattgggcgg atccaggaac aaaaagttgg ggggattcaa    840

cataccgagt acactggcat aaacacatca tctcagtatt aaactatgct aaaatgctat    900

taagagacct ttagcacctc ttatcttatc aaccatggtg aaaaaattga aggggggact    960

caggggggta tccatgggtc cgatgggtgc aggggggact gagtcccccc tgcacccacg   1020

ttgaatccgc cctggcatgc gtataagctg tcacagccat ttctaggtgc ttgtgcttag   1080

ttgggtgatg tcagcttaat ttgtcttttc tatgtcgtca tcgattttct aagaaacgaa   1140

aaatagccta tttatgtgct ccagaatttg atgatccctg gcccttcatt tgctgaaatt   1200

agcctatttg ttggttgccc ttcagttttt tcccagctta tgttgttgca atgtgtggct   1260

atgcctcgtt ttgtgcccta taatttatta tttgcaattc atttttgtac atgacttaaa   1320

atgacactag agcaacatgc actgattggt tatcctataa tcatttatgt agttctgttc   1380

attttatcat gctagctcat gtcattttca tcttcaggcc tctggcacag ttccacctga   1440

gcgtcctgga gctggttcat ccttgctgaa tgcagatgtt tcacacatag gcgctcctaa   1500
```

```
ttccatcgga ggtacttatc ttatctggtt acattttcag attgttatga aactacccaa   1560
atatcctgca caattgcatg ggattaaatt ttagtttctt tgaaatagaa gtagagttgt   1620
attgctgtca cgtcatcaaa tagttctgaa gctatgaata aataagttcc gcatttgtta   1680
gtgattcttt gaacattaga attgttatgc ttaagtagat agggttatgt ttgtttggag   1740
ttcccttaaa tcatttcatt gctgactgcc agctggcagg agcatttgtt gttgccttga   1800
ccatgaatga agaccttcct gttctgagtg ctcacaagaa aacatatttt gattaatgca   1860
ccttgaatcc ttaggatctt gcaaagatgg gcacttagct ttagaattga gtagtactta   1920
aatagctgtt gttatcatga tttgtcctgt agtgaaatgt cgacaaaaca ggaatgctac   1980
ttttgacttc tgatatttca tgcctggctt tacttatgct ctgtttggaa catgggcaca   2040
tatcaggcaa tgctactcca gttcaaaaca tgctaagtgg cccaagtggg ggatcgggct   2100
cacagttggt acagaatgtt gatgtccttg taaagcagcc caccagctct tcatcaaggg   2160
agcagtcaga tgatgatgac atgaagggag aagctgagac cactggaact gcaagacctg   2220
ctgatcaaag attacaacga aggtgatcat tcattgcttc cttgtaatat agattctgta   2280
cataattaac ctacctcgtc atgcatgcat gtgtcctatt ttcaccttag ccctttcagt   2340
tggatttcca ctttcatccg gtagcctttc agtttcctat tgcatcgcat atatgatctt   2400
ttacctacca tattagttct ctgtgtgcca tactcagtgc ttagtgtctc gagcaagaga   2460
ggaatttgta tggctattac acgtagcact ttgctctcta cttgtttatt gacataagca   2520
atttgggatg aattaaatct gagttcacat catattcctt atgtcacaag tttctgaaac   2580
cgattgtatc tagtatctgg ttgatgcacc cccatcttgg atttgcaaat caaagttata   2640
ctccctagag agctttacct ttcataaagc aattacccca ataaaccacg gatttgatag   2700
ctattgacta tgattaccag aattcatttg gcagctattt tctcaattta agtttggtat   2760
tagtctcagt tggctgtaaa ataatgtcac ggtagggtac atgtatgtgc agcatacaag   2820
gtatgggtga gttatgatat ggacagtgtg tacaccccac atttgctcac taaaatcaaa   2880
atattcaaac gtcacgtgat gatatggtgg attgcattat accttgtatt gtttattatg   2940
ttacttgtgc tagacaataa tataggctgt tcttttgggt gattttgtat gaagatgttg   3000
agcaagcact tctcgatata atgctagttt tgttgacctg ttccaggaag caatccaatc   3060
gggagtcagc caggcgctca agaagcagaa aggcagctca cttgaatgag ctggaggcac   3120
aggtgtgata gttcacatag ttattttcga taagacataa aatcctaaat tactggctac   3180
tgacttcagt tatggattta cttgttacag gtatcgcaat taagagtcga gaactcctcg   3240
ctgttaaggc gtcttgctga tgttaaccag aagtacaatg atgctgctgt tgacaataga   3300
gtgctaaaag cagatgttga gaccttgaga gcaaaggtat gctatatatg ccttttgcaa   3360
tatgcatccc atggattgct actttggctt gtttcaaact ttcaacgtga cttgtgtacc   3420
ctgttattag aagaataatc ccgcctacca ttatactcta taaatcacca tttggccagt   3480
ccaaacatga ttattaaatc aggtcaatct gaacattgaa atgtatcaaa aattcgcagg   3540
tgaagatggc agaggactcg gtgaagcggg tgacaggcat gaacgcgttg tttcccgccg   3600
cttctgatat gtcatccctc agcatgccat tcaacagctc cccatctgaa gcaacgtcag   3660
acgctgctgt tcccatccaa gatgacccga acaattactt cgctactaac aacgacatcg   3720
gaggtaacaa caactacatg cccgacatac cttcttcggc tcaggaggac gaggacttcg   3780
tcaatggcgc tctggctgcc ggcaagattg gccggccagc ctcgctgcag cgggtggcga   3840
gcctggagca tctccagaag aggatgtgcg gtgggccggc ttcgtctggg tcgacgtcct   3900
```

```
ga                                                                  3902


<210> SEQ ID NO 23
<211> LENGTH: 11
<212> TYPE: PRT
<213> ORGANISM: Artificial Sequence
<220> FEATURE:
<223> OTHER INFORMATION: N-terminal sequence of recombinant hTF
<220> FEATURE:
<221> NAME/KEY: UNSURE
<222> LOCATION: (9)..(9)
<223> OTHER INFORMATION: Xaa = unknown amino acid

<400> SEQUENCE: 23

Val Pro Asp Lys Thr Val Arg Trp Xaa Ala Val
1               5                   10


<210> SEQ ID NO 24
<211> LENGTH: 697
<212> TYPE: PRT
<213> ORGANISM: Mus musculus
<220> FEATURE:
<223> OTHER INFORMATION: murine transferrin GenBank AAL34533.1

<400> SEQUENCE: 24

Met Arg Phe Ala Val Gly Ala Leu Leu Ala Cys Ala Ala Leu Gly Leu
1               5                   10                  15

Cys Leu Ala Val Pro Asp Lys Thr Val Lys Trp Cys Ala Val Ser Glu
            20                  25                  30

His Glu Asn Thr Lys Cys Ile Ser Phe Arg Asp His Met Lys Thr Val
        35                  40                  45

Leu Pro Pro Asp Gly Pro Arg Leu Ala Cys Val Lys Lys Thr Ser Tyr
    50                  55                  60

Pro Asp Cys Ile Lys Ala Ile Ser Ala Ser Glu Ala Asp Ala Met Thr
65                  70                  75                  80

Leu Asp Gly Gly Trp Val Tyr Asp Ala Gly Leu Thr Pro Asn Asn Leu
                85                  90                  95

Lys Pro Val Ala Ala Glu Phe Tyr Gly Ser Val Glu His Pro Gln Thr
            100                 105                 110

Tyr Tyr Tyr Ala Val Ala Val Val Lys Lys Gly Thr Asp Phe Gln Leu
        115                 120                 125

Asn Gln Leu Glu Gly Lys Lys Ser Cys His Thr Gly Leu Gly Arg Ser
    130                 135                 140

Ala Gly Trp Val Ile Pro Ile Gly Leu Leu Phe Cys Lys Leu Ser Glu
145                 150                 155                 160

Pro Arg Ser Pro Leu Glu Lys Ala Val Ser Ser Phe Phe Ser Gly Ser
                165                 170                 175

Cys Val Pro Cys Ala Asp Pro Val Ala Phe Pro Lys Leu Cys Gln Leu
            180                 185                 190

Cys Pro Gly Cys Gly Cys Ser Ser Thr Gln Pro Phe Phe Gly Tyr Val
        195                 200                 205

Gly Ala Phe Lys Cys Leu Lys Asp Gly Gly Gly Asp Val Ala Phe Val
    210                 215                 220

Lys His Thr Thr Ile Phe Glu Val Leu Pro Glu Lys Ala Asp Arg Asp
225                 230                 235                 240

Gln Tyr Glu Leu Leu Cys Leu Asp Asn Thr Arg Lys Pro Val Asp Gln
                245                 250                 255

Tyr Glu Asp Cys Tyr Leu Ala Arg Ile Pro Ser His Ala Val Val Ala
```

```
            260                 265                 270

Arg Lys Asn Asn Gly Lys Glu Asp Leu Ile Trp Glu Ile Leu Lys Val
        275                 280                 285

Ala Gln Glu His Phe Gly Lys Gly Lys Ser Lys Asp Phe Gln Leu Phe
    290                 295                 300

Ser Ser Pro Leu Gly Lys Asp Leu Leu Phe Lys Asp Ser Ala Phe Gly
305                 310                 315                 320

Leu Leu Arg Val Pro Pro Arg Met Asp Tyr Arg Leu Tyr Leu Gly His
                325                 330                 335

Asn Tyr Val Thr Ala Ile Arg Asn Gln Gln Glu Gly Val Cys Pro Glu
            340                 345                 350

Gly Ser Ile Asp Asn Ser Pro Val Lys Trp Cys Ala Leu Ser His Leu
        355                 360                 365

Glu Arg Thr Lys Cys Asp Glu Trp Ser Ile Ile Ser Glu Gly Lys Ile
    370                 375                 380

Glu Cys Glu Ser Ala Glu Thr Thr Glu Asp Cys Ile Glu Lys Ile Val
385                 390                 395                 400

Asn Gly Glu Ala Asp Ala Met Thr Leu Asp Gly Gly His Ala Tyr Ile
                405                 410                 415

Ala Gly Gln Cys Gly Leu Val Pro Val Met Ala Glu Tyr Tyr Glu Ser
            420                 425                 430

Ser Asn Cys Ala Ile Pro Ser Gln Gln Gly Ile Phe Pro Lys Gly Tyr
        435                 440                 445

Tyr Ala Val Ala Val Val Lys Ala Ser Asp Thr Ser Ile Thr Trp Asn
    450                 455                 460

Asn Leu Lys Gly Lys Lys Ser Cys His Thr Gly Val Asp Arg Thr Ala
465                 470                 475                 480

Gly Trp Asn Ile Pro Met Gly Met Leu Tyr Asn Arg Ile Asn His Cys
                485                 490                 495

Lys Phe Asp Glu Phe Phe Ser Gln Gly Cys Ala Pro Gly Tyr Glu Lys
            500                 505                 510

Asn Ser Thr Leu Cys Asp Leu Cys Ile Gly Pro Leu Lys Cys Ala Pro
        515                 520                 525

Asn Asn Lys Glu Glu Tyr Asn Gly Tyr Thr Gly Ala Phe Arg Cys Leu
    530                 535                 540

Val Glu Lys Gly Asp Val Ala Phe Val Lys His Gln Thr Val Leu Asp
545                 550                 555                 560

Asn Thr Glu Gly Lys Asn Pro Ala Glu Trp Ala Lys Asn Leu Lys Gln
                565                 570                 575

Glu Asp Phe Glu Leu Leu Cys Pro Asp Gly Thr Arg Lys Pro Val Lys
            580                 585                 590

Asp Phe Ala Ser Cys His Leu Ala Gln Ala Pro Asn His Val Val Val
        595                 600                 605

Ser Arg Lys Glu Lys Ala Ala Arg Val Lys Ala Val Leu Thr Ser Gln
    610                 615                 620

Glu Thr Leu Phe Gly Gly Ser Asp Cys Thr Gly Asn Phe Cys Leu Phe
625                 630                 635                 640

Lys Ser Thr Thr Lys Asp Leu Leu Phe Arg Asp Asp Thr Lys Cys Phe
                645                 650                 655

Val Lys Leu Pro Glu Gly Thr Thr Pro Glu Lys Tyr Leu Gly Ala Glu
            660                 665                 670

Tyr Met Gln Ser Val Gly Asn Met Arg Lys Cys Ser Thr Ser Arg Leu
        675                 680                 685
```

```
Leu Glu Ala Cys Thr Phe His Lys Ser
    690                 695


<210> SEQ ID NO 25
<211> LENGTH: 698
<212> TYPE: PRT
<213> ORGANISM: Rattus norvegicus
<220> FEATURE:
<223> OTHER INFORMATION: rat transferrin GenBank BAA07458.1

<400> SEQUENCE: 25

Met Arg Phe Ala Val Gly Ala Leu Leu Ala Cys Ala Ala Leu Gly Leu
1               5                   10                  15

Cys Leu Ala Val Pro Asp Lys Thr Val Lys Trp Cys Ala Val Ser Glu
            20                  25                  30

His Glu Asn Thr Lys Cys Ile Ser Phe Arg Asp His Met Lys Thr Val
        35                  40                  45

Leu Pro Ala Asp Gly Pro Arg Leu Ala Cys Val Lys Lys Thr Ser Tyr
    50                  55                  60

Gln Asp Cys Ile Lys Ala Ile Ser Gly Gly Glu Ala Asp Ala Ile Thr
65                  70                  75                  80

Leu Asp Gly Gly Trp Val Tyr Asp Ala Gly Leu Thr Pro Asn Asn Leu
                85                  90                  95

Lys Pro Val Ala Ala Glu Phe Tyr Gly Ser Leu Glu His Pro Gln Thr
            100                 105                 110

His Tyr Leu Ala Val Ala Val Val Lys Lys Gly Thr Asp Phe Gln Leu
        115                 120                 125

Asn Gln Leu Gln Gly Lys Lys Ser Cys His Thr Gly Leu Gly Arg Ser
    130                 135                 140

Ala Gly Trp Ile Ile Pro Ile Gly Leu Leu Phe Cys Asn Leu Pro Glu
145                 150                 155                 160

Pro Arg Lys Pro Leu Glu Lys Ala Val Ala Ser Phe Phe Ser Gly Ser
                165                 170                 175

Cys Val Pro Cys Ala Asp Pro Val Ala Phe Pro Gln Leu Cys Gln Leu
            180                 185                 190

Cys Pro Gly Cys Gly Cys Ser Pro Thr Gln Pro Phe Phe Gly Tyr Val
        195                 200                 205

Gly Ala Phe Lys Cys Leu Arg Asp Gly Gly Gly Asp Val Ala Phe Val
    210                 215                 220

Lys His Thr Thr Ile Phe Glu Val Leu Pro Gln Lys Ala Asp Arg Asp
225                 230                 235                 240

Gln Tyr Glu Leu Leu Cys Leu Asp Asn Thr Arg Lys Pro Val Asp Gln
                245                 250                 255

Tyr Glu Asp Cys Tyr Leu Ala Arg Ile Pro Ser His Ala Val Val Ala
            260                 265                 270

Arg Asn Gly Asp Gly Lys Glu Asp Leu Ile Trp Glu Ile Leu Lys Val
        275                 280                 285

Ala Gln Glu His Phe Gly Lys Gly Lys Ser Lys Asp Phe Gln Leu Phe
    290                 295                 300

Gly Ser Pro Leu Gly Lys Asp Leu Leu Phe Lys Asp Ser Ala Phe Gly
305                 310                 315                 320

Cys Tyr Gly Val Pro Pro Arg Met Asp Tyr Arg Leu Tyr Leu Gly His
                325                 330                 335

Ser Tyr Val Thr Ala Ile Arg Asn Gln Arg Glu Gly Val Cys Pro Glu
            340                 345                 350
```

```
Ala Ser Ile Asp Ser Ala Pro Val Lys Trp Cys Ala Leu Ser His Gln
        355                 360                 365

Glu Arg Ala Lys Cys Asp Glu Trp Ser Val Thr Ser Asn Gly Gln Ile
    370                 375                 380

Glu Cys Glu Ser Ala Glu Ser Thr Glu Asp Cys Ile Asp Lys Ile Val
385                 390                 395                 400

Asn Gly Glu Ala Asp Ala Met Ser Leu Asp Gly Gly His Ala Tyr Ile
                405                 410                 415

Ala Gly Gln Cys Gly Leu Val Pro Val Met Ala Glu Asn Tyr Asp Ile
            420                 425                 430

Ser Ser Cys Thr Asn Pro Gln Ser Asp Val Phe Pro Lys Gly Tyr Tyr
        435                 440                 445

Ala Val Ala Val Val Lys Ala Ser Asp Ser Ser Ile Asn Trp Asn Asn
    450                 455                 460

Leu Lys Gly Lys Lys Ser Cys His Thr Gly Val Asp Arg Thr Ala Gly
465                 470                 475                 480

Trp Asn Ile Pro Met Gly Leu Leu Phe Ser Arg Ile Asn His Cys Lys
                485                 490                 495

Phe Asp Glu Phe Phe Ser Gln Gly Cys Ala Pro Gly Tyr Lys Lys Asn
            500                 505                 510

Ser Thr Leu Cys Asp Leu Cys Ile Gly Pro Ala Lys Cys Ala Pro Asn
        515                 520                 525

Asn Arg Glu Gly Tyr Asn Gly Tyr Thr Gly Ala Phe Gln Cys Leu Val
    530                 535                 540

Glu Lys Gly Asp Val Ala Phe Val Lys His Gln Thr Val Leu Glu Asn
545                 550                 555                 560

Thr Asn Gly Lys Asn Thr Ala Ala Trp Ala Lys Asp Leu Lys Gln Glu
                565                 570                 575

Asp Phe Gln Leu Leu Cys Pro Asp Gly Thr Lys Lys Pro Val Thr Glu
            580                 585                 590

Phe Ala Thr Cys His Leu Ala Gln Ala Pro Asn His Val Val Val Ser
        595                 600                 605

Arg Lys Glu Lys Ala Ala Arg Val Ser Thr Val Leu Thr Ala Gln Lys
    610                 615                 620

Asp Leu Phe Trp Lys Gly Asp Lys Asp Cys Thr Gly Asn Phe Cys Leu
625                 630                 635                 640

Phe Arg Ser Ser Thr Lys Asp Leu Leu Phe Arg Asp Asp Thr Lys Cys
                645                 650                 655

Leu Thr Lys Leu Pro Glu Gly Thr Thr Tyr Glu Glu Tyr Leu Gly Ala
            660                 665                 670

Glu Tyr Leu Gln Ala Val Gly Asn Ile Arg Lys Cys Ser Thr Ser Arg
        675                 680                 685

Leu Leu Glu Ala Cys Thr Phe His Lys Ser
    690                 695
```

<210> SEQ ID NO 26
<211> LENGTH: 715
<212> TYPE: PRT
<213> ORGANISM: Sus scrofa
<220> FEATURE:
<223> OTHER INFORMATION: porcine transferrin GenBank CAQ34904.1

<400> SEQUENCE: 26

```
Met Arg Leu Ala Val Arg Ala Leu Leu Ala Cys Ala Val Leu Gly Leu
1               5                   10                  15
```

-continued

```
Ser Leu Ala Val Ala Gln Lys Thr Val Arg Trp Cys Thr Ile Ser Asn
            20                  25                  30

Gln Glu Ala Asn Lys Cys Ser Ser Phe Arg Glu Asn Met Ser Lys Ala
        35                  40                  45

Val Lys Asn Gly Pro Leu Val Ser Cys Val Lys Lys Ser Ser Tyr Leu
    50                  55                  60

Asp Cys Ile Lys Ala Ile Arg Asp Lys Glu Ala Asp Ala Val Thr Leu
65                  70                  75                  80

Asp Ala Gly Leu Val Phe Glu Ala Gly Leu Ala Pro Tyr Asn Leu Lys
                85                  90                  95

Pro Val Val Ala Glu Phe Tyr Gly Gln Lys Asp Asn Pro Gln Thr His
            100                 105                 110

Tyr Tyr Ala Val Ala Val Val Lys Lys Gly Ser Asn Phe Gln Trp Asn
        115                 120                 125

Gln Leu Gln Gly Lys Arg Ser Cys His Thr Gly Leu Gly Arg Ser Ala
    130                 135                 140

Gly Trp Ile Ile Pro Met Gly Leu Leu Tyr Asp Gln Leu Pro Glu Pro
145                 150                 155                 160

Arg Lys Pro Ile Glu Lys Ala Val Ala Ser Phe Phe Ser Ser Ser Cys
                165                 170                 175

Val Pro Cys Ala Asp Pro Val Asn Phe Pro Lys Leu Cys Gln Gln Cys
            180                 185                 190

Ala Gly Lys Gly Ala Glu Lys Cys Ala Cys Ser Asn His Glu Pro Tyr
        195                 200                 205

Phe Gly Tyr Ala Gly Ala Phe Asn Cys Leu Lys Glu Asp Ala Gly Asp
    210                 215                 220

Val Ala Phe Val Lys His Ser Thr Val Leu Glu Asn Leu Pro Asp Lys
225                 230                 235                 240

Ala Asp Arg Asp Gln Tyr Glu Leu Leu Cys Arg Asp Asn Thr Arg Arg
                245                 250                 255

Pro Val Asp Asp Tyr Glu Asn Cys Tyr Leu Ala Gln Val Pro Ser His
            260                 265                 270

Ala Val Val Ala Arg Ser Val Asp Gly Gln Glu Asp Ser Ile Trp Glu
        275                 280                 285

Leu Leu Asn Gln Ala Gln Glu His Phe Gly Arg Asp Lys Ser Pro Asp
    290                 295                 300

Phe Gln Leu Phe Ser Ser Ser His Gly Lys Asp Leu Leu Phe Lys Asp
305                 310                 315                 320

Ser Ala Asn Gly Phe Leu Arg Ile Pro Ser Lys Met Asp Ser Ser Leu
                325                 330                 335

Tyr Leu Gly Tyr Gln Tyr Val Thr Ala Leu Arg Asn Leu Arg Glu Glu
            340                 345                 350

Ile Ser Pro Asp Ser Ser Lys Asn Glu Cys Lys Lys Val Arg Trp Cys
        355                 360                 365

Ala Ile Gly His Glu Glu Thr Gln Lys Cys Asp Ala Trp Ser Ile Asn
    370                 375                 380

Ser Gly Gly Lys Ile Glu Cys Val Ser Ala Glu Asn Thr Glu Asp Cys
385                 390                 395                 400

Ile Ala Lys Ile Val Lys Gly Glu Ala Asp Ala Met Ser Leu Asp Gly
                405                 410                 415

Gly Tyr Ile Tyr Ile Ala Gly Lys Cys Gly Leu Val Pro Val Leu Ala
            420                 425                 430
```

```
Glu Asn Tyr Lys Thr Glu Gly Glu Asn Cys Val Asn Thr Pro Glu Lys
        435                 440                 445

Gly Tyr Leu Ala Val Ala Val Val Lys Lys Ser Ser Gly Pro Asp Leu
    450                 455                 460

Asn Trp Asn Asn Leu Lys Gly Lys Lys Ser Cys His Thr Ala Val Asp
465                 470                 475                 480

Arg Thr Ala Gly Trp Asn Ile Pro Met Gly Leu Leu Tyr Asn Lys Ile
                485                 490                 495

Asn Ser Cys Lys Phe Asp Gln Phe Phe Gly Glu Gly Cys Ala Pro Gly
            500                 505                 510

Ser Gln Arg Asn Ser Ser Leu Cys Ala Leu Cys Ile Gly Ser Glu Arg
        515                 520                 525

Ala Pro Gly Arg Glu Cys Leu Ala Asn Asn His Glu Arg Tyr Tyr Gly
    530                 535                 540

Tyr Thr Gly Ala Phe Arg Cys Leu Val Glu Lys Gly Asp Val Ala Phe
545                 550                 555                 560

Val Lys Asp Gln Val Val Gln Gln Asn Thr Asp Gly Lys Asn Lys Asp
                565                 570                 575

Asp Trp Ala Lys Asp Leu Lys Gln Met Asp Phe Glu Leu Leu Cys Gln
            580                 585                 590

Asn Gly Ala Arg Glu Pro Val Asp Asn Ala Glu Asn Cys His Leu Ala
        595                 600                 605

Arg Ala Pro Asn His Ala Val Val Ala Arg Asp Asp Lys Val Thr Cys
    610                 615                 620

Val Ala Glu Glu Leu Leu Lys Gln Gln Ala Gln Phe Gly Arg His Val
625                 630                 635                 640

Thr Asp Cys Ser Ser Ser Phe Cys Met Phe Lys Ser Asn Thr Lys Asp
                645                 650                 655

Leu Leu Phe Arg Asp Asp Thr Gln Cys Leu Ala Arg Val Gly Lys Thr
            660                 665                 670

Thr Tyr Glu Ser Tyr Leu Gly Ala Asp Tyr Ile Thr Ala Val Ala Asn
        675                 680                 685

Leu Arg Lys Cys Ser Thr Ser Lys Leu Leu Glu Ala Cys Thr Phe His
    690                 695                 700

Ser Ala Lys Asn Pro Arg Val Glu Thr Thr Thr
705                 710                 715


<210> SEQ ID NO 27
<211> LENGTH: 710
<212> TYPE: PRT
<213> ORGANISM: Macaca cyclopsis
<220> FEATURE:
<223> OTHER INFORMATION: macaque transferrin GenBank ACB11584.1

<400> SEQUENCE: 27

Met Lys Leu Val Phe Leu Ala Leu Leu Phe Leu Gly Thr Leu Gly Leu
1               5                   10                  15

Cys Leu Ala Ala Arg Arg Arg Ser Val Arg Trp Cys Ala Val Ser Lys
            20                  25                  30

Pro Glu Ala Thr Lys Cys Ser Gln Trp Gln Arg Asn Leu Arg Arg Val
        35                  40                  45

Arg Gly Pro Pro Val Ser Cys Ile Lys Arg Ala Ser Pro Thr Asn Cys
    50                  55                  60

Ile Gln Ala Ile Ala Ala Asn Arg Ala Asp Ala Met Thr Leu Asp Gly
65                  70                  75                  80
```

-continued

```
Gly Leu Met Tyr Glu Ala Gly Leu Ala Pro Tyr Lys Leu Arg Pro Val
                85                  90                  95

Ala Ala Glu Val Tyr Gly Thr Glu Glu Lys Pro Arg Thr His Tyr Tyr
            100                 105                 110

Ala Val Ala Val Val Lys Lys Gly Gly Arg Phe Gln Leu Asn Glu Leu
        115                 120                 125

Gln Gly Leu Lys Ser Cys His Thr Gly Leu Asn Arg Thr Ala Gly Trp
    130                 135                 140

Ile Val Pro Ile Gly Met Leu Arg Pro Phe Leu Asn Trp Thr Gly Pro
145                 150                 155                 160

Pro Glu Ala Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Val Gly Thr Gly Glu Asn Lys Cys Ala Phe Ser Ser Gln Arg Pro Tyr
        195                 200                 205

Phe Gly Tyr Ser Gly Ala Phe Lys Cys Leu Arg Asp Gly Thr Gly Asp
    210                 215                 220

Val Ala Phe Ile Arg Glu Ser Thr Val Phe Glu Asp Leu Ser Asp Pro
225                 230                 235                 240

Ala Glu Arg Asp Asn Tyr Glu Leu Leu Cys Pro Asp Asn Thr Arg Lys
                245                 250                 255

Pro Val Asp Lys Phe Lys Glu Cys His Leu Ala Arg Val Pro Ser His
            260                 265                 270

Ala Val Val Ala Arg Ser Val Asn Gly Lys Glu Asp Ala Ile Trp Glu
        275                 280                 285

Leu Leu Arg Gln Ala Gln Glu Lys Phe Gly Lys Asp Lys Ser Pro Glu
    290                 295                 300

Phe Gln Leu Phe Gly Ser Pro Arg Gly Gln Lys Asp Leu Leu Phe Lys
305                 310                 315                 320

Asp Ser Ala Ile Gly Phe Ser Arg Val Pro Leu Arg Ile Asp Ser Gly
                325                 330                 335

Leu Tyr Leu Gly Ser Gly His Leu Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Gln Gln Glu Leu Glu Lys Cys Asp Gln Trp Ser Ala Leu Ser
    370                 375                 380

Glu Gly Asn Val Asn Cys Ser Leu Ala Ser Thr Ala Asp Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Glu Pro Gln Gln Ser Ser Gly Pro Asp Pro Asn Cys Val Asp
        435                 440                 445

Arg Pro Val Glu Gly Tyr Leu Ala Val Ala Val Val Arg Asn Ser Asp
    450                 455                 460

Ala Gly Leu Thr Trp Asn Ser Leu Lys Gly Lys Lys Ser Cys His Thr
465                 470                 475                 480

Ala Val Asp Arg Thr Ala Gly Trp Asn Ile Pro Ile Gly Leu Leu Phe
                485                 490                 495

Asn Gln Thr Gly Ser Cys Lys Phe Asp Glu Tyr Phe Ser Gln Ser Cys
```

```
            500                 505                 510

Ala Pro Gly Ala Asp Pro Arg Ser Asn Leu Cys Ala Leu Cys Ile Gly
        515                 520                 525

Asn Glu Gln Gly Glu Asp Lys Cys Val Pro Asn Thr Asn Glu Arg Tyr
    530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Lys
                565                 570                 575

Asn Thr Asp Ala Trp Ala Lys Asp Leu Lys Leu Asn Asp Phe Glu Leu
            580                 585                 590

Leu Cys Leu Asp Gly Thr Arg Lys Pro Val Thr Glu Ala Arg Ser Cys
        595                 600                 605

His Leu Ala Met Ala Pro Asn His Ala Val Val Ser Arg Thr Glu Lys
    610                 615                 620

Val Glu Arg Leu Lys Gln Val Leu Phe Asp Gln Gln Ala Lys Phe Gly
625                 630                 635                 640

Lys Asn Gly Ser Asp Cys Pro Gly Thr Phe Cys Leu Phe Gln Ser Lys
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Thr
        675                 680                 685

Ala Ile Thr Asn Leu Lys Lys Cys Ser Ser Ser Pro Leu Leu Glu Ala
    690                 695                 700

Cys Ala Phe Leu Gln Lys
705                 710
```

<210> SEQ ID NO 28
<211> LENGTH: 2938
<212> TYPE: DNA
<213> ORGANISM: Oryza sativa japonica
<220> FEATURE:
<223> OTHER INFORMATION: alpha-amylase (RAmy3D) gene

<400> SEQUENCE: 28

```
gatcttcaac cacctgtgct agctactcca ctgctccata ggcaatcatc aatcagtaat     60

ccgttctgaa aagaagatat aggtgtgcgc aatcaggaac gttctagttc gtgctagaaa    120

tcagcagctc ctaagttagc atctcgatga acttaaatgc tcgctgcggg cgtccggcgg    180

agatgaagtt tgtgataaac ttggtcatga cattcatata tgtgcctggt gtacggagta    240

gttcatcagc aaacatacac ctacttctac cttatccatt tggattgctc atggcggctt    300

tgatatggaa tttgtaatga acttggttat gacttatgac atactgatac tcgtaacatt    360

catagatact gacataaatt catcaactac aatagatgag atggctagtc ttagtagaac    420

agtagtctct ctttccggct tgctccattg gctgatgacg atgaacaact cggactcatt    480

gattccagca ttatctgatt ctcgcatttc gaggtccgga ttagggtctc accgagatgt    540

ggatagaatt gccatgtcag gaattgaagg aggacgagcc atatgtgcat atacatgacg    600

ggagatcaag cggccagtca agaggctaac tgcaacccta ttatatacga tcagcctgct    660

agaacacgta gcactgtctt ttttgtctga actctgaaga tgaaaggttc agagaaatgg    720

ctcgccttat ccaagccggc gatggatgga ggaggaggta gccggcgccc gcctcaggca    780

gtcgtcgcga tcacgccgcc gcatcccgtc gccttggaga ccgggccccg acgcggccga    840
```

-continued

```
cgcggcgcct acgtggccat gctttattgc cttatccata tccacgccat ttattgtggt    900

cgtctctcct gatcattctc attcccctgc cacggtgacc gtgcccccgg tgttctatat    960

atgccccccg acgtcgaggt cattcgccac gaacacatcg atcatccatc atctacaaga   1020

gatcgatcag tagtggttag cagcaactca ctatcgaaca cggtttcagc ttacacagat   1080

atgaagaaca ccagcagctt gtgtttgctg ctcctcgtgg tgctctgcag cttgacctgt   1140

aactcgggtc aagcacaggt cctcttccag gtacgtagta ctctactacc catcactttc   1200

tgtgaagact tttgctgaag aaacacatta gaattttgag atatttatgt gtgatcgatt   1260

gatcacttac ctacttataa catgcatcat gcagggtttc aactgggagt cgtggaagca   1320

gcagggtggc tggtacaaca tgttgaaagg ccaagtcgac gacatcgcca aggccggggt   1380

cacccacgtc tggctgccgc cgccgtcgca ctccgtggcg ccgcaggggt acatgccggg   1440

gcgtctctac gacctggacg cgtccaagta cggcacggcg gcggagctca agtcgctgat   1500

cgcggcgttc cacgggaagg gcgtccagtg cgtcgccgac gtcgtgatca accaccggtg   1560

cgccgagaag aaggacgccc gcggcgtgta ctgcgtgttc gagggcggga cgcccgaccg   1620

cctcgactgg ggccccggca tgatctgcag cgacgacacg cagtactccg acggcacggg   1680

ccaccgcgac accggcgagg ggttcggcgc ggcgcccgac atcgaccacc tcaacccgcg   1740

cgtccagcgg gagctcaccg actggctcaa ctggctcaag tccgacgtcg gcttcgacgg   1800

ctggcgcctc gacttcgcca agggatactc cacggacatc gctaagatgt acgtcgagag   1860

ctgcaagccg ggcttcgtcg tcgccgagat atggaactcg ctgagctaca acggcgacgg   1920

caagccggcg gccaaccagg accagggccg gcaggagctg gtgaactggg tgaacgccgt   1980

cggcgggccg gcgatgacgt tcgacttcac caccaagggc ctcctgcagg cgggcgtcca   2040

gggcgagctg tggcggctgc gcgacggcaa cggcaaggcg cccggcatga tcgggtggct   2100

gccagagaag gccgtcacgt tcgtcgacaa ccacgacacc ggctcgacgc agaagctttg   2160

gccgttcccc tccgacaagg tcatgcaggg ctacgcctac atcctcaccc accccggagt   2220

cccctgcatc gtaagcaaac catgcattat agtattatat accatgtcct gattaacctc   2280

caccgtacac gtgtcctgat gaacgcttct tgtggcagtt ctacgaccac atgttcgact   2340

ggaacctgaa gcaggagata accgcgctgg cggcgatcag ggagaggaac ggcatcaacg   2400

ccgggagcaa gctccggatc gtcgtcgccg acgccgacgc atacgtcgcc gtcgtcgacg   2460

agaaggtcat ggtgaagatc gggacgaggt acgacgtggg caacgcggtg ccgtcggatt   2520

tccatcagac ggtgcacggc aaggactaca gcgtctggga gaaggggtcc ctccgcgtcc   2580

cggcggggcg gcacctatag cgggctcaag ccctaaactg aacgggatag tcatgctcaa   2640

accagtttct acacggcaag aatttactga ttcttatact tttgcagtca attaaattat   2700

ggtttttata tatgtaattt tgtatccgat tgtagcgttc gaataagtag gcaggctctc   2760

tagcctctag gttaattgcg gggcatatgt agcttgccag ttaattgtgt ttgtatcacg   2820

cagtttgtaa ccgttggtgc aatatataat gtcaggttca ggatgcagta aaaaatcata   2880

ctgcaccgat cagtgagttt ttatatactg gttttaaaag tgagcacaag tactagtt     2938
```